US012780853B2

(12) United States Patent
Liu et al.

(10) Patent No.: US 12,780,853 B2
(45) Date of Patent: Nov. 3, 2026

(54) INDOLE-CONTAINING MACROCYCLIC COMPOUNDS AND USES THEREOF

(71) Applicant: JIANGSU AOSAIKANG PHARMACEUTICAL CO., LTD., Nanjing (CN)

(72) Inventors: Yingchun Liu, Shanghai (CN); Lihong Hu, Shanghai (CN); Charles Z. Ding, Shanghai (CN)

(73) Assignee: JIANGSU AOSAIKANG PHARMACEUTICAL CO., LTD., Nanjing (CN)

( * ) Notice: Subject to any disclaimer, the term of this patent is extended or adjusted under 35 U.S.C. 154(b) by 302 days.

(21) Appl. No.: 18/832,613

(22) PCT Filed: Jan. 16, 2023

(86) PCT No.: PCT/CN2023/072315

§ 371 (c)(1),
(2) Date: Aug. 22, 2024

(87) PCT Pub. No.: WO2023/143169

PCT Pub. Date: Aug. 3, 2023

(65) Prior Publication Data

US 2025/0109156 A1 Apr. 3, 2025

(30) Foreign Application Priority Data

Jan. 28, 2022 (CN) ......................... 202210108561.8
Apr. 29, 2022 (CN) ......................... 202210476398.0
Jun. 13, 2022 (CN) ......................... 202210667398.9
Jul. 27, 2022 (CN) ......................... 202210894289.0

(51) Int. Cl.
*C07F 9/6561* (2006.01)
*A61K 31/675* (2006.01)

(52) U.S. Cl.
CPC .......... *C07F 9/6561* (2013.01); *A61K 31/675* (2013.01)

(58) Field of Classification Search
CPC ............................ C07F 9/6561; A61K 31/675
See application file for complete search history.

(56) References Cited

U.S. PATENT DOCUMENTS

2017/0327496 A1* 11/2017 Ciblat .................. C07D 401/04
2019/0241541 A1 8/2019 Ciblat et al.

FOREIGN PATENT DOCUMENTS

CN 112661745 A 4/2021
WO 2019/143719 A1 7/2019
WO WO-2019143730 A1 7/2019
WO 2020/093006 A1 5/2020
WO 2023/116761 A1 6/2023

OTHER PUBLICATIONS

Aug. 5, 2025 First Office Action issued in Japanese Patent Application No. 2024-545010.
Sep. 24, 2025 European Search Report issued in European Patent Application No. 23746051.4.
Apr. 21, 2023 International Search Report issued in International Patent Application No. PCT/CN2023/072315.
Apr. 21, 2023 Written Opinion of the International Searching Authority issued in International Patent Application No. PCT/CN2023/072315.
May 11, 2026 First Office Action issued in Korean Patent Application No. 10-2024-7028777.

* cited by examiner

*Primary Examiner* — Timothy R Rozof
(74) *Attorney, Agent, or Firm* — Harness, Dickey & Pierce, P.L.C.

(57) ABSTRACT

The present invention provides indole-containing macrocyclic compounds and the uses thereof, and particularly relates to compounds represented by formula (II) or pharmaceutically acceptable salts thereof.

(II)

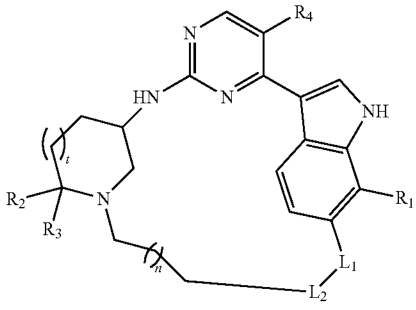

20 Claims, No Drawings

INDOLE-CONTAINING MACROCYCLIC COMPOUNDS AND USES THEREOF

CROSS-REFERENCE TO RELATED APPLICATIONS

The present application is a U.S. National Phase Application under 35 U.S.C. 371 of International Application No. PCT/CN2023/072315, filed on Jan. 16, 2023, which claims the benefit of Chinese patent application CN202210108561.8, filed on Jan. 28, 2022, Chinese patent application CN202210476398.0, filed on Apr. 29, 2022, Chinese patent application CN202210667398.9, filed on Jun. 13, 2022, and Chinese patent application CN202210894289.0, filed on Jul. 27, 2022. The entire disclosures of the above Chinese patent applications are incorporated herein by reference in their entirety.

The present application claims the right of the following priorities:

CN202210108561.8, application date: Jan. 28, 2022;
CN202210476398.0, application date: Apr. 29, 2022;
CN202210667398.9, application date: Jun. 13, 2022;
CN202210894289.0, application date: Jul. 27, 2022.

TECHNICAL FIELD

The present disclosure discloses a class of indole-containing macrocyclic compounds and uses thereof, and specifically discloses a compound of formula (II) and a pharmaceutically acceptable salt thereof.

BACKGROUND

Cell cycle refers to the continuous dynamic process that normally continuously dividing cells undergo from the end of the previous mitosis to the end of the next mitosis. The cell cycle of mammals consists of four phases: G1 phase (prophase of DNA synthesis), S phase (DNA synthesis phase), G2 phase (anaphase of DNA synthesis), and M phase (mitosis phase), respectively. M phase is followed by cytokinesis, forming two daughter cells. Although newborn cells generated through cell cycle division will re-enter the cell cycle, at a certain time point in the late G1 phase (known as the restriction point or R point), the cell cycle regulatory mechanism will determine the ultimate fate of the cell: continue to participate in the cell cycle, or exit the active proliferative state and enter a quiescent (G0) state. The regulation of the cell cycle is mainly influenced by a series of serine/threonine kinases, which are also known as cyclin-dependent kinases (CDKs). They achieve the purpose of regulating the cell cycle by binding to their corresponding regulatory subunits, cyclins.

Abnormal proliferation of cancer cells and dysregulation of normal cell cycles are common features of all types of cancer. Therefore, inhibitors of key cell cycle regulators have become an attractive and novel anti-tumor target. CDK7 is an important member of the CDKs family, also known as CDK activating kinase (CAK). CDK7 primarily regulates the cell cycle through two indirect ways: first, the CDK7-cyclin H binary complex or the CDK7-cyclin H-MAT1 ternary complex is activated by phosphorylation to generate active CAK, which can further phosphorylate the threonine residues in the active regions of CDKs (1, 2, 3, 4, 6), thereby activating their activity and leading the initiation, progression, and termination of the cell cycle; secondly, the phosphorylated CDK7-cyclin H-MAT1 complex can phosphorylate the large subunit of the carboxyl-terminal domain (CTD) of the large subunit of RNA polymerase II (RNAP II), thereby promoting promoter clearance and inducing the start of transcription. Additionally, the CDK7-cyclin H-MAT1 complex is also a subunit component of transcription factor IIH (TFIIH), participating in type II transcription and nucleotide excision repair. Therefore, inhibiting the phosphorylation of the active region of CDK7 can inhibit its role in regulating the cell cycle, both blocking the leading role of CDKs (1, 2, 3, 4, 6) in the cell cycle and affecting the transcription process, thereby achieving the purpose of inhibiting tumor cell proliferation. Based on the important regulatory role of CDK7 in the cell cycle and transcription, designing CDK7 inhibitors with novel scaffold structures targeting CDK7 has become one of the hotspots in the field of anti-tumor drug research.

Currently, several CDK7 small molecule inhibitors have entered clinical research stages for cancer treatment, such as SY-5609 from Syros Pharmaceuticals and CT-7001. These CDK7 inhibitors can inhibit the activation of CDK proteins as well as the phosphorylation of the C-terminal domain of RNA polymerase II, thereby affecting transcription regulation.

Although many efforts have been made in developing CDK7 inhibitors for the treatment of cancer and other diseases, no drugs against this target have been marketed so far. Among the varieties under investigation, SY-5609 has very high activity but a low maximum tolerated dose in clinical trials, while CT-7001 has good in vitro activity but poor metabolic stability, limiting its further development as a drug. Therefore, there is still an urgent need to develop novel, safer, and more effective CDK7 inhibitors that can treat various cancers, including breast cancer.

CONTENT OF THE PRESENT INVENTION

The present disclosure provides a compound of formula (II) or a pharmaceutically acceptable salt thereof, (II)

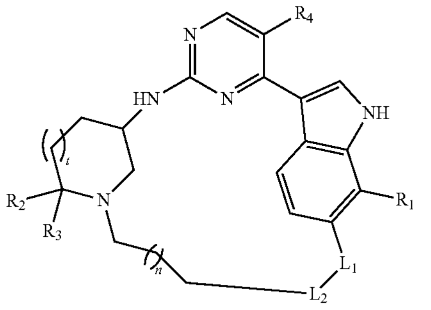

wherein $R_1$ is selected from H, CN, F, Cl, Br, I, $C_{1-3}$ alkyl, —$OC_{1-3}$ alkyl, $C_{3-6}$ cycloalkyl, $S(O)_mR_a$, $P(X)R_cR_d$, $C(O)R_a$, $S(O)_mNR_aR_b$, and $C(O)NR_aR_b$, and the $C_{1-3}$ alkyl, —$OC_{1-3}$ alkyl, and $C_{3-6}$ cycloalkyl are optionally substituted by 1, 2, or 3 R;

$R_a$ is selected from $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl, $R_b$ is selected from H and $C_{1-3}$ alkyl, and the $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl are optionally substituted by 1, 2, or 3 R;

$R_c$ and $R_d$ are independently selected from $C_{1-3}$ alkyl and $OC_{1-3}$ alkyl, or $R_c$ and $R_d$ together with the P atom to which they are attached form a 4- to 6-membered heterocycloalkyl ring, and the —$OC_{1-3}$ alkyl, $C_{1-3}$ alkyl, and 4- to 6-membered heterocycloalkyl ring are optionally substituted by 1, 2, or 3 R;

X is selected from O and S;

$L_1$ is selected from —$CH_2$—, —O—, —$NR_e$—, —C(O)—, —$S(O)_q$—, and —P(O)—;

$L_2$ is selected from —$CH_2$—, —O—, and —$NR_e$—;

$R_e$ is selected from H and $C_{1-3}$ alkyl, and the $C_{1-3}$ alkyl is optionally substituted by 1, 2, or 3 R;

$R_2$ and $R_3$ are each independently selected from H, $C_{1-3}$ alkyl, and $C_{2-4}$ alkenyl, or $R_2$ and $R_3$ together with the C atom to which they are attached form a $C_{3-6}$ cycloalkyl ring or a 3- to 6-membered heterocycloalkyl ring, and the $C_{1-3}$ alkyl, $C_{2-4}$ alkenyl, $C_{3-6}$ cycloalkyl ring, and 3- to 6-membered heterocycloalkyl ring are optionally substituted by 1, 2, or 3 R;

$R_4$ is selected from $C_{1-3}$ haloalkyl, CN, F, Cl, Br, and I,

R is independently selected from F, Cl, Br, $NH_2$, and CN;

n is selected from 0, 1, 2, 3, 4, and 5;

m and q are independently selected from 1 and 2;

t is selected from 0, 1, 2, and 3.

The present disclosure provides a compound of formula (I) or a pharmaceutically acceptable salt thereof, (I)

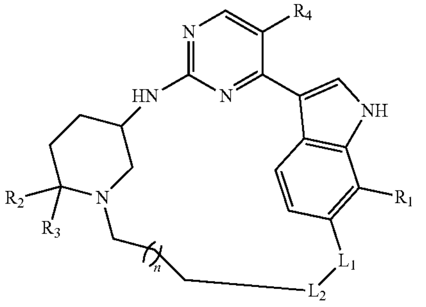

wherein $R_1$ is selected from H, CN, F, Cl, Br, I, $C_{1-3}$ alkyl, —$OC_{1-3}$ alkyl, $C_{3-6}$ cycloalkyl, $S(O)_mR_a$, $P(X)R_cR_d$, $C(O)R_a$, $S(O)_mNR_aR_b$, and $C(O)NR_aR_b$, and the $C_{1-3}$ alkyl, —$OC_{1-3}$ alkyl, and $C_{3-6}$ cycloalkyl are optionally substituted by 1, 2, or 3 R;

$R_a$ is selected from $C_{1-3}$ alkyl, —$OC_{1-3}$ alkyl, —$NHC_{1-3}$ alkyl, —$N(C_{1-3}\ alkyl)_2$, and $C_{3-6}$ cycloalkyl, $R_b$ is selected from H and $C_{1-3}$ alkyl, and the $C_{1-3}$ alkyl, —$OC_{1-3}$ alkyl, —$NHC_{1-3}$ alkyl, —$N(C_{1-3}\ alkyl)_2$, and $C_{3-6}$ cycloalkyl are optionally substituted by 1, 2, or 3 R;

$R_c$ and $R_d$ are independently selected from $C_{1-3}$ alkyl and $OC_{1-3}$ alkyl, or $R_c$ and $R_d$ together with the P atom to which they are attached form a 4- to 6-membered heterocycloalkyl ring, and the —$OC_{1-3}$ alkyl, $C_{1-3}$ alkyl, and 4- to 6-membered heterocycloalkyl ring are optionally substituted by 1, 2, or 3 R;

X is selected from O and S;

$L_1$ is selected from —$CH_2$—, —O—, —$NR_e$—, —C(O)—, —$S(O)_q$—, and —P(O)—;

$L_2$ is selected from —$CH_2$—, —O—, and —$NR_e$—;

$R_e$ is selected from H and $C_{1-3}$ alkyl, and the $C_{1-3}$ alkyl is optionally substituted by 1, 2, or 3 R;

$R_2$ and $R_3$ are each independently selected from H, $C_{1-3}$ alkyl, and $C_{2-4}$ alkenyl, or $R_2$ and $R_3$ together with the C atom to which they are attached form a $C_{3-6}$ cycloalkyl ring or a 3- to 6-membered heterocycloalkyl ring, and the $C_{1-3}$ alkyl, $C_{2-4}$ alkenyl, $C_{3-6}$ cycloalkyl ring, and 3- to 6-membered heterocycloalkyl ring are optionally substituted by 1, 2, or 3 R;

$R_4$ is selected from $C_{1-3}$ haloalkyl, CN, F, Cl, Br, and I,

R is independently selected from F, Cl, Br, $NH_2$, and CN;

n is selected from 0, 1, 2, 3, 4, and 5;

m and q are independently selected from 1 and 2.

In some technical embodiments of the present disclosure, the $R_1$ is selected from H, and other variables are as defined in the present disclosure.

In some technical embodiments of the present disclosure, the $R_1$ is selected from CN, and other variables are as defined in the present disclosure.

In some technical embodiments of the present disclosure, the $R_1$ is selected from F, and other variables are as defined in the present disclosure.

In some technical embodiments of the present disclosure, the $R_1$ is selected from Cl, and other variables are as defined in the present disclosure.

In some technical embodiments of the present disclosure, the $R_1$ is selected from Br, and other variables are as defined in the present disclosure.

In some technical embodiments of the present disclosure, the $R_1$ is selected from $C_{1-3}$ alkyl, and the $C_{1-3}$ alkyl is optionally substituted by 1, 2, or 3 R, and other variables are as defined in the present disclosure.

In some technical embodiments of the present disclosure, the $R_1$ is selected from $CH_3$, $CH_2CH_3$, $CH_2CH_2CH_3$, $CH(CH_3)_2$, $CH_2F$, $CHF_2$, $CF_3$, $CH_2Cl$, $CHCl_2$, and $CCl_3$, and other variables are as defined in the present disclosure.

In some technical embodiments of the present disclosure, the $R_1$ is selected from —$OC_{1-3}$ alkyl, and the —$OC_{1-3}$ alkyl is optionally substituted by 1, 2, or 3 R, and other variables are as defined in the present disclosure.

In some technical embodiments of the present disclosure, the $R_1$ is selected from —$OCH_3$, —$OCH_2CH_3$, —$OCH_2CH_2CH_3$, —$OCH(CH_3)_2$, —$OCH_2F$, —$OCHF_2$, —$OCF_3$, —$OCH_2Cl$, —$OCHCl_2$, and —$OCCl_3$, and other variables are as defined in the present disclosure.

In some technical embodiments of the present disclosure, the $R_1$ is selected from $C_{3-6}$ cycloalkyl, and the $C_{3-6}$ cycloalkyl is selected from

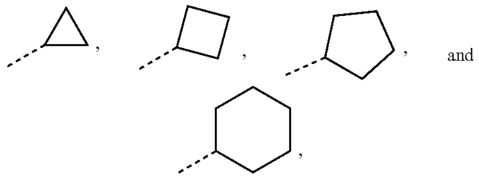

and the

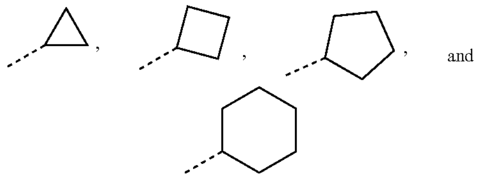

are optionally substituted by 1, 2, or 3 R.

In some technical embodiments of the present disclosure, the $R_1$ is selected from $S(O)_mR_a$, and the $S(O)_mR_a$ is selected from

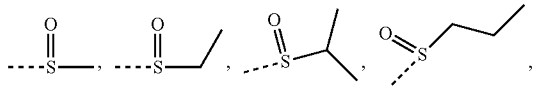

,

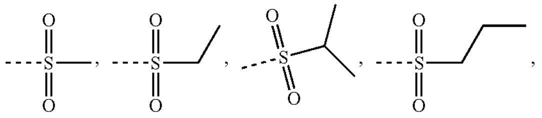

,

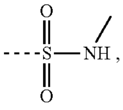

and

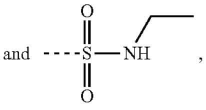

, and other variables are as defined in the present disclosure.

In some technical embodiments of the present disclosure, the $R_1$ is selected from $S(O)_mNR_aR_b$, and the $S(O)_mNR_aR_b$ is selected from

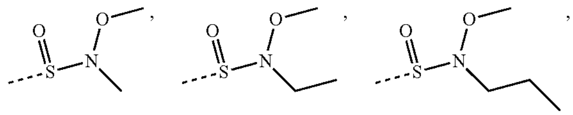

,

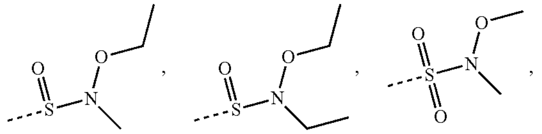

,

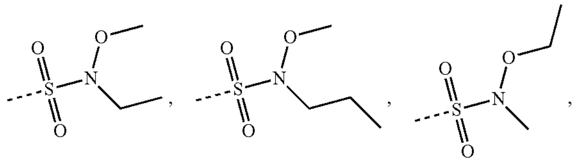

,

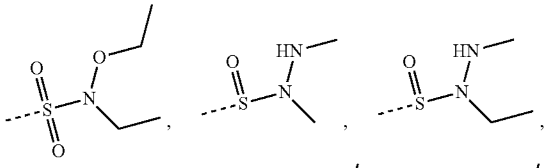

,

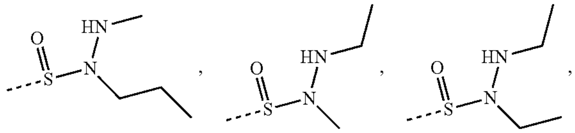

,

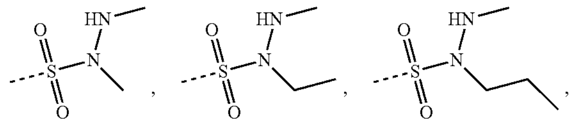

,

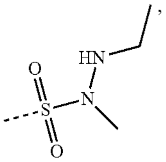

and

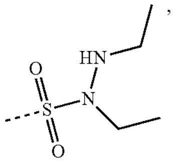

, and other variables are as defined in the present disclosure.

In some technical embodiments of the present disclosure, the $R_1$ is selected from $P(X)R_cR_d$, the $P(X)R_cR_d$ is selected from

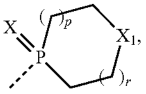

, $X_1$ is selected from $CH_2$, O, and NH, p is selected from 0 and 1, r is selected from 0 and 1, and other variables are as defined in the present disclosure.

In some technical embodiments of the present disclosure, the

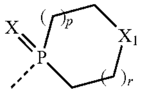

is selected from

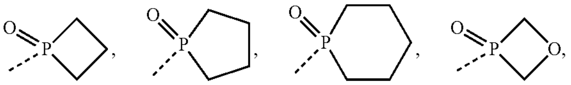

,

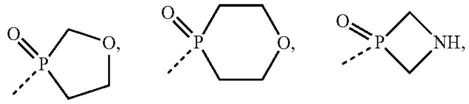

,

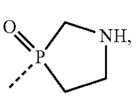

and

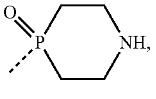

, and other variables are as defined in the present disclosure.

In some technical embodiments of the present disclosure, the $R_1$ is selected from

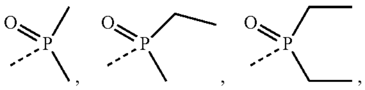

,

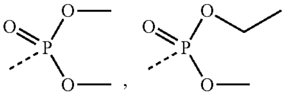

and

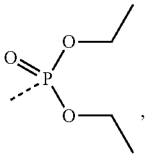

, and other variables are as defined in the present disclosure.

In some technical embodiments of the present disclosure, the $R_1$ is selected from $C(O)R_a$, and the $C(O)R_a$ is selected from

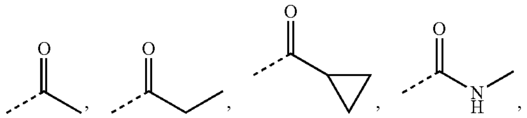

and

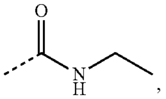

, and other variables are as defined in the present disclosure.

In some technical embodiments of the present disclosure, the $R_1$ is selected from $C(O)NR_aR_b$, and the $C(O)NR_aR_b$ is selected from

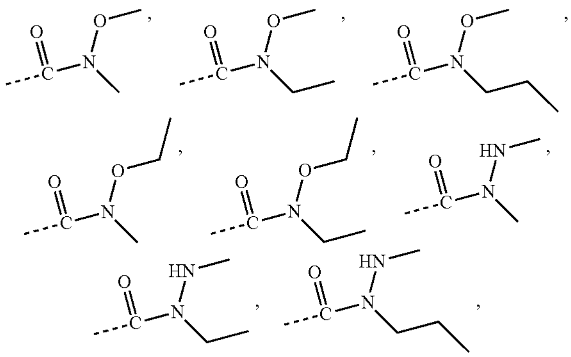

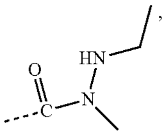

and

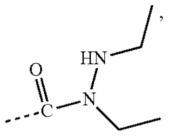

and other variables are as defined in the present disclosure.

In some technical embodiments of the present disclosure, the $R_1$ is selected from

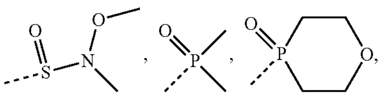

and

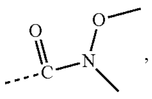

and other variables are as defined in the present disclosure.

In some technical embodiments of the present disclosure, the $R_2$ and $R_3$ are each independently selected from H, methyl, ethyl, n-propyl, and isopropyl, or $R_2$ and $R_3$ together with the C atom to which they are attached form a cyclopropyl ring, a cyclobutyl ring, a cyclopentyl ring, and a cyclohexyl ring, and other variables are as defined in the present disclosure.

In some technical embodiments of the present disclosure, the $R_2$ and $R_3$ are each independently selected from H and methyl, and other variables are as defined in the present disclosure.

In some technical embodiments of the present disclosure, the $R_2$ and $R_3$ together with the C atom to which they are attached form a cyclopropyl ring, and other variables are as defined in the present disclosure.

In some technical embodiments of the present disclosure, the $L_1$ is selected from $—CH_2—$, $—O—$, $—NR_e—$, $—C(O)—$, $—S(O)—$, $—S(O)_2—$, and $—P(O)—$, and other variables are as defined in the present disclosure.

In some technical embodiments of the present disclosure, the structural moiety

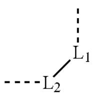

is selected from

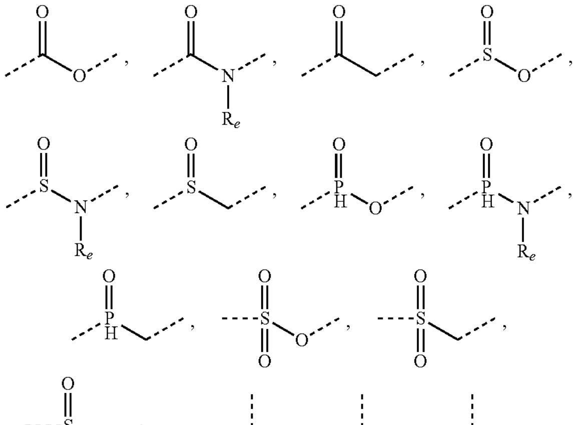

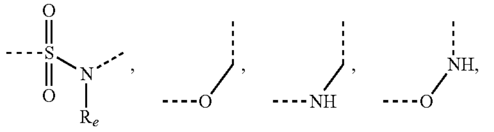

and

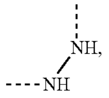

and other variables are as defined in the present disclosure.

In some technical embodiments of the present disclosure, the structural moiety

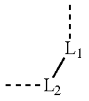

is selected from

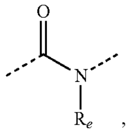

and other variables are as defined in the present disclosure.

In some technical embodiments of the present disclosure, the structural moiety

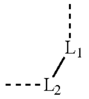

is selected from

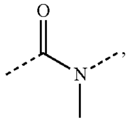

and other variables are as defined in the present disclosure.

In some technical embodiments of the present disclosure, the structural moiety

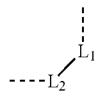

is selected from

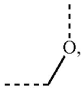

and other variables are as defined in the present disclosure.

In some technical embodiments of the present disclosure, the compound is as shown in formulae (I-1), (I-2), and (II-1), (I-1)

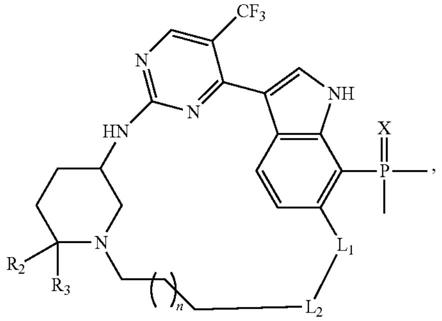

(I-2)

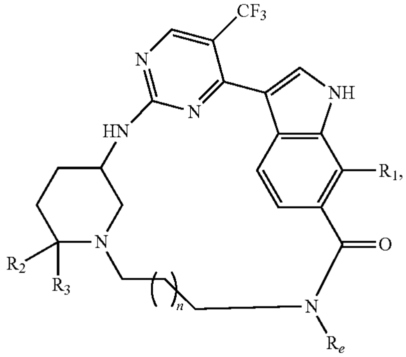

and (II-1)

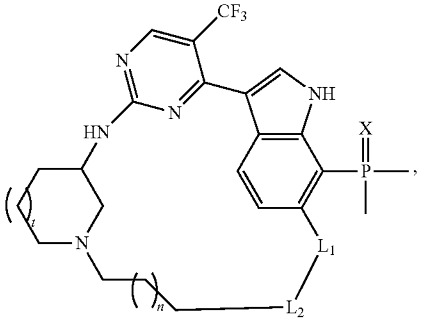

and other variables are as defined in the present disclosure.

In some technical embodiments of the present disclosure, the compound is as shown in formulae (II-1-1) and (II-1-2), (II-1-1)

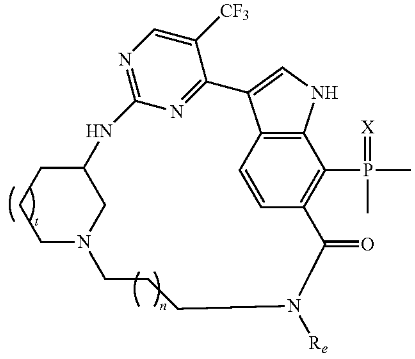

and (II-1-2)

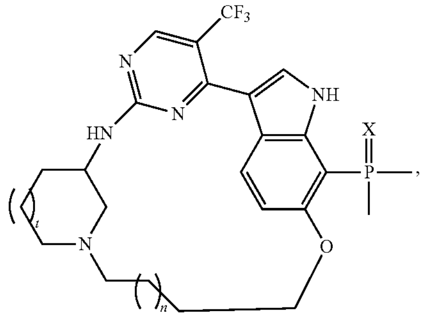

and other variables are as defined in the present disclosure.

In some technical embodiments of the present disclosure, the $R_e$ is selected from hydrogen, methyl, ethyl, and propyl, and other variables are as defined in the present disclosure.

The present disclosure provides a compound of formula (I-A) or a pharmaceutically acceptable salt thereof, (I-A)

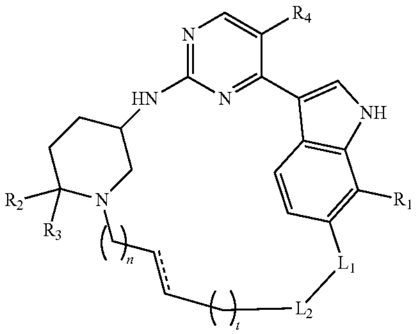

wherein

 is selected from a single bond and a double bond;

$R_1$ is selected from H, CN, F, Cl, Br, I, $C_{1-3}$ alkyl, —$OC_{1-3}$ alkyl, $C_{3-6}$ cycloalkyl, $S(O)_mR_a$, $P(X)R_cR_d$, $C(O)R_a$, $S(O)_mNR_aR_b$, and $C(O)NR_aR_b$, and the $C_{1-3}$ alkyl, —$OC_{1-3}$ alkyl, and $C_{3-6}$ cycloalkyl are optionally substituted by 1, 2, or 3 R;

$R_a$ is selected from $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl, $R_b$ is selected from H and $C_{1-3}$ alkyl, and the $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl are optionally substituted by 1, 2, or 3 R;

$R_c$ and $R_d$ are independently selected from $C_{1-3}$ alkyl and $OC_{1-3}$ alkyl, or $R_c$ and $R_d$ together with the P atom to which they are attached form a 4- to 6-membered heterocycloalkyl ring, and the —$OC_{1-3}$ alkyl, $C_{1-3}$ alkyl, and 4- to 6-membered heterocycloalkyl ring are optionally substituted by 1, 2, or 3 R;

X is selected from O and S;

$L_1$ is selected from —$CH_2$—, —O—, —$NR_e$—, —C(O)—, —$S(O)_q$—, and —P(O)—;

$L_2$ is selected from absent, —$CH_2$—, —O—, and —$NR_e$—;

$R_e$ is selected from H and $C_{1-3}$ alkyl, and the $C_{1-3}$ alkyl is optionally substituted by 1, 2, or 3 R;

$R_2$ and $R_3$ are each independently selected from H, $C_{1-3}$ alkyl, and $C_{2-4}$ alkenyl, or $R_2$ and $R_3$ together with the C atom to which they are attached form a $C_{3-6}$ cycloalkyl ring or a 3- to 6-membered heterocycloalkyl ring, and the $C_{1-3}$ alkyl, $C_{2-4}$ alkenyl, $C_{3-6}$ cycloalkyl ring, and 3- to 6-membered heterocycloalkyl ring are optionally substituted by 1, 2, or 3 R;

$R_4$ is selected from $C_{1-3}$ haloalkyl, CN, F, Cl, Br, and I,

R is independently selected from F, Cl, Br, $NH_2$, and CN;

n is selected from 1, 2, and 3;

t is selected from 0, 1, 2, and 3;

m and q are independently selected from 0, 1, and 2.

The present disclosure provides a compound of formula (I-B) or a pharmaceutically acceptable salt thereof, (I-B)

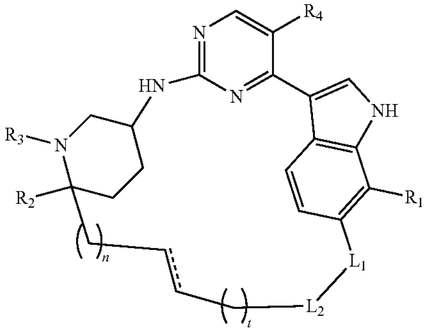

wherein

 is selected from a single bond and a double bond;

$R_1$ is selected from H, CN, F, Cl, Br, I, $C_{1-3}$ alkyl, —$OC_{1-3}$ alkyl, $C_{3-6}$ cycloalkyl, $S(O)_mR_a$, $P(X)R_cR_d$, $C(O)R_a$, $S(O)_mNR_aR_b$, and $C(O)NR_aR_b$, and the $C_{1-3}$ alkyl, —$OC_{1-3}$ alkyl, and $C_{3-6}$ cycloalkyl are optionally substituted by 1, 2, or 3 R;

$R_a$ is selected from $C_{1-3}$ alkyl, —$OC_{1-3}$ alkyl, —$NHC_{1-3}$ alkyl, —$N(C_{1-3}\ alkyl)_2$, and $C_{3-6}$ cycloalkyl, $R_b$ is selected from H and $C_{1-3}$ alkyl, and the $C_{1-3}$ alkyl, —$OC_{1-3}$ alkyl, —$NHC_{1-3}$ alkyl, —$N(C_{1-3}\ alkyl)_2$, and $C_{3-6}$ cycloalkyl are optionally substituted by 1, 2, or 3 R;

$R_c$ and $R_d$ are independently selected from $C_{1-3}$ alkyl and $OC_{1-3}$ alkyl, or $R_c$ and $R_d$ together with the P atom to which they are attached form a 4- to 6-membered heterocycloalkyl ring, and the —$OC_{1-3}$ alkyl, $C_{1-3}$ alkyl, and 4- to 6-membered heterocycloalkyl ring are optionally substituted by 1, 2, or 3 R;

X is selected from O and S;

$L_1$ is selected from —$CH_2$—, —O—, —$NR_e$—, —C(O)—, —$S(O)_q$—, and —P(O)—;

$L_2$ is selected from absent, —$CH_2$—, —O—, and —$NR_e$—;

$R_e$ is selected from H and $C_{1-3}$ alkyl, and the $C_{1-3}$ alkyl is optionally substituted by 1, 2, or 3 R;

$R_2$ and $R_3$ are each independently selected from H, $C_{1-3}$ alkyl, and $C_{2-4}$ alkenyl, or $R_2$ and $R_3$ together with the atom to which they are attached form a 3- to 6-membered heterocycloalkyl ring, and the $C_{1-3}$ alkyl, $C_{2-4}$ alkenyl, and 3- to 6-membered heterocycloalkyl ring are optionally substituted by 1, 2, or 3 R;

$R_4$ is selected from $C_{1-3}$ haloalkyl, CN, F, Cl, Br, and I,

R is independently selected from F, Cl, Br, $NH_2$, and CN;

n is selected from 1, 2, and 3;

t is selected from 0, 1, 2, and 3;

m and q are independently selected from 0, 1, and 2.

In some technical embodiments of the present disclosure, the $R_1$ is selected from H, and other variables are as defined in the present disclosure.

In some technical embodiments of the present disclosure, the $R_1$ is selected from CN, and other variables are as defined in the present disclosure.

In some technical embodiments of the present disclosure, the $R_1$ is selected from F, and other variables are as defined in the present disclosure.

In some technical embodiments of the present disclosure, the $R_1$ is selected from Cl, and other variables are as defined in the present disclosure.

In some technical embodiments of the present disclosure, the $R_1$ is selected from Br, and other variables are as defined in the present disclosure.

In some technical embodiments of the present disclosure, the $R_1$ is selected from $C_{1-3}$ alkyl, and the $C_{1-3}$ alkyl is optionally substituted by 1, 2, or 3 R, and other variables are as defined in the present disclosure.

In some technical embodiments of the present disclosure, the $R_1$ is selected from $CH_3$, $CH_2CH_3$, $CH_2CH_2CH_3$, $CH(CH_3)_2$, $CH_2F$, $CHF_2$, $CF_3$, $CH_2Cl$, $CHCl_2$, and $CCl_3$, and other variables are as defined in the present disclosure.

In some technical embodiments of the present disclosure, the $R_1$ is selected from —$OC_{1-3}$ alkyl, and the —$OC_{1-3}$ alkyl is optionally substituted by 1, 2, or 3 R, and other variables are as defined in the present disclosure.

In some technical embodiments of the present disclosure, the $R_1$ is selected from —$OCH_3$, —$OCH_2CH_3$, —$OCH_2CH_2CH_3$, —$OCH(CH_3)_2$, —$OCH_2F$, —$OCHF_2$, —$OCF_3$, —$OCH_2Cl$, —$OCHCl_2$, and —$OCCl_3$, and other variables are as defined in the present disclosure.

In some technical embodiments of the present disclosure, the $R_1$ is selected from $C_{3-6}$ cycloalkyl, and the $C_{3-6}$ cycloalkyl is selected from

, , 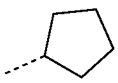, and 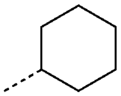, and the

, , 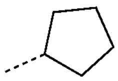, and

-continued

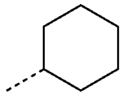

are optionally substituted by 1, 2, or 3 R.

In some technical embodiments of the present disclosure, the $R_1$ is selected from $S(O)_mR_a$, and the $S(O)_mR_a$ is selected from

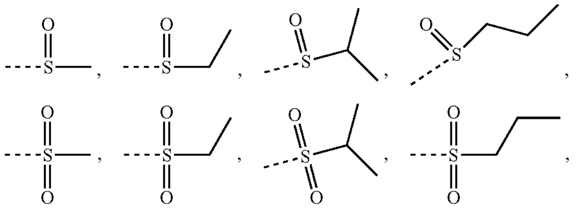

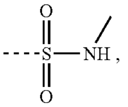

and

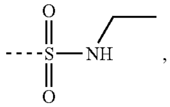

and other variables are as defined in the present disclosure.

In some technical embodiments of the present disclosure, the $R_1$ is selected from $S(O)_mNR_aR_b$, and the $S(O)_mNR_aR_b$ is selected from

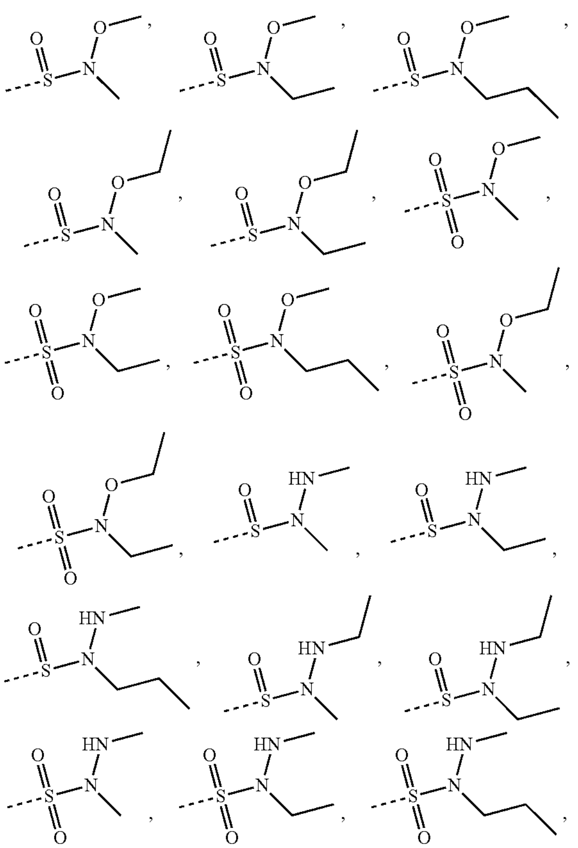

-continued

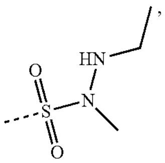

and

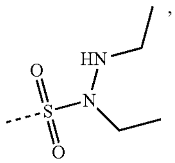

and other variables are as defined in the present disclosure.

In some technical embodiments of the present disclosure, the $R_1$ is selected from $P(X)R_cR_d$, the $P(X)R_cR_d$ is selected from

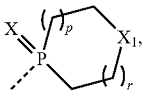

$X_1$ is selected from $CH_2$, O, and NH, p is selected from 0 and 1, r is selected from 0 and 1, and other variables are as defined in the present disclosure.

In some technical embodiments of the present disclosure, the

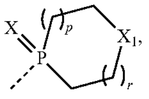

is selected from

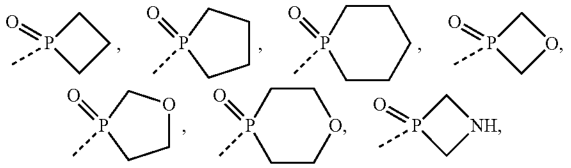

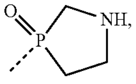

and

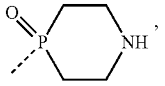

and other variables are as defined in the present disclosure.

In some technical embodiments of the present disclosure, the $R_1$ is selected from

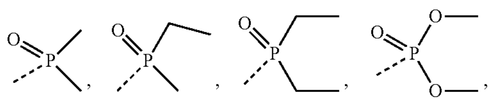

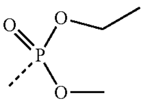

and

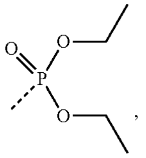

and other variables are as defined in the present disclosure.

In some technical embodiments of the present disclosure, the $R_1$ is selected from $C(O)R_a$, and the $C(O)R_a$ is selected from

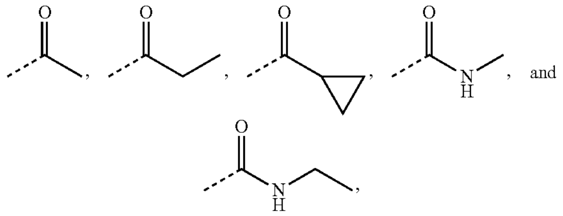

and and other variables are as defined in the present disclosure.

In some technical embodiments of the present disclosure, the $R_1$ is selected from $C(O)NR_aR_b$, and the $C(O)NR_aR_b$ is selected from

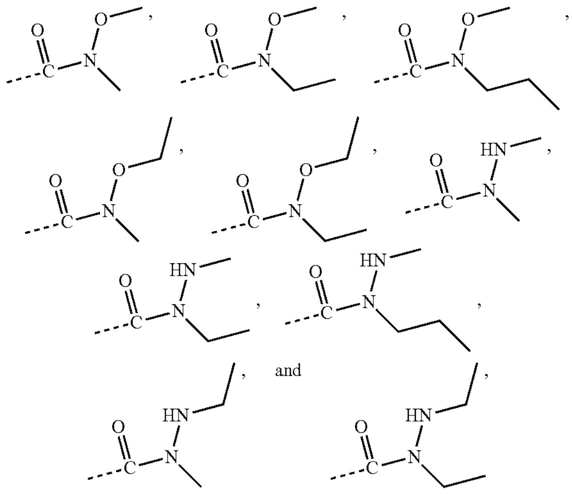

and and other variables are as defined in the present disclosure.

In some technical embodiments of the present disclosure, the $R_1$ is selected from

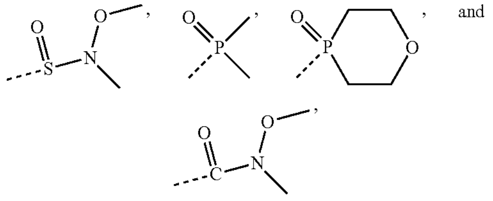

and and other variables are as defined in the present disclosure.

In some technical embodiments of the present disclosure, the $R_2$ and $R_3$ are each independently selected from H, methyl, ethyl, n-propyl, and isopropyl, or $R_2$ and $R_3$ together with the C atom to which they are attached form a cyclopropyl ring, a cyclobutyl ring, a cyclopentyl ring, and a cyclohexyl ring, and other variables are as defined in the present disclosure.

In some technical embodiments of the present disclosure, the $R_2$ and $R_3$ are each independently selected from H and methyl, and other variables are as defined in the present disclosure.

In some technical embodiments of the present disclosure, the $R_2$ and $R_3$ together with the C atom to which they are attached form a cyclopropyl ring, and other variables are as defined in the present disclosure.

In some technical embodiments of the present disclosure, the $L_1$ is selected from $-CH_2-$, $-O-$, $-NR_e-$, $-C(O)-$, $-S(O)-$, $-S(O)_2-$, and $-P(O)-$, and other variables are as defined in the present disclosure.

In some technical embodiments of the present disclosure, the structural moiety

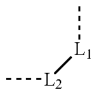

is selected from

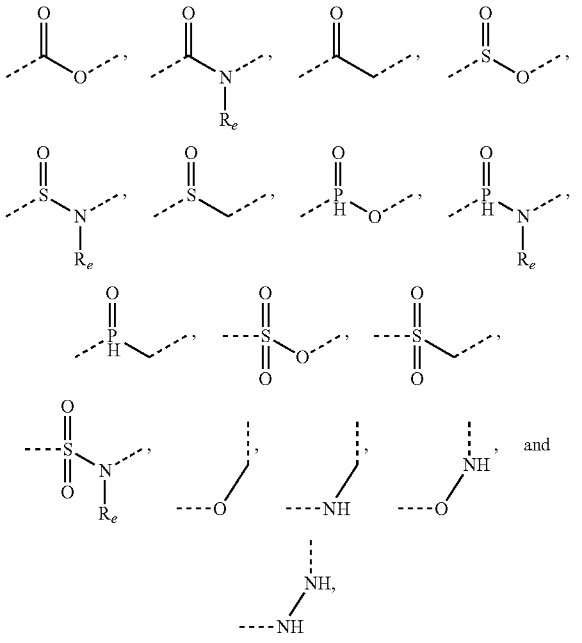

and and other variables are as defined in the present disclosure.

In some technical embodiments of the present disclosure, the structural moiety

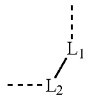

is selected from

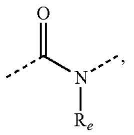

and other variables are as defined in the present disclosure.

In some technical embodiments of the present disclosure, the structural moiety

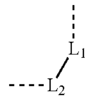

is selected from

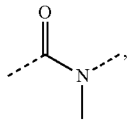

and other variables are as defined in the present disclosure.

In some technical embodiments of the present disclosure, the compound is as shown in formulae (I-A-1) and (I-A-2), (I-A-1)

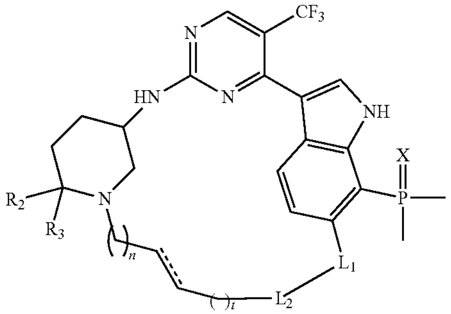

and (I-A-2)

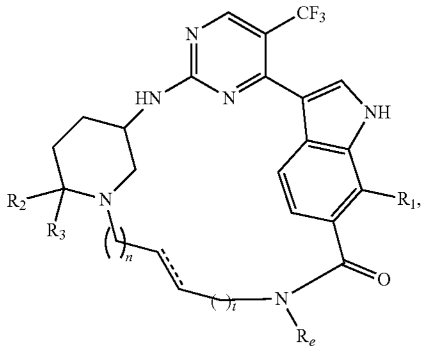

and other variables are as defined in the present disclosure.

In some technical embodiments of the present disclosure, the compound is as shown in formulae (I-A-3) and (I-A-4), (I-A-3)

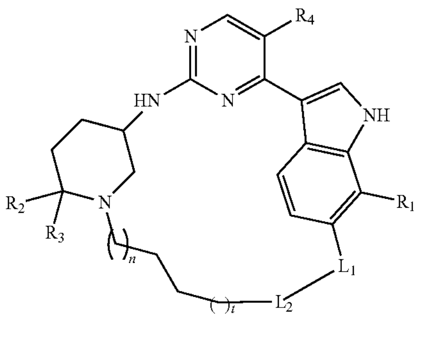

and

-continued (I-A-4)

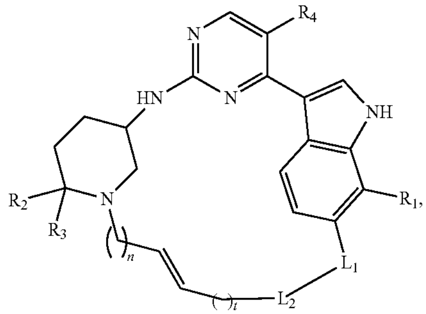

and other variables are as defined in the present disclosure.

In some technical embodiments of the present disclosure, the n=1, t=0, and other variables are as defined in the present disclosure.

In some technical embodiments of the present disclosure, the n=1, t=1, and other variables are as defined in the present disclosure.

In some technical embodiments of the present disclosure, the n=1, t=2, and other variables are as defined in the present disclosure.

In some technical embodiments of the present disclosure, the n=2, t=0, and other variables are as defined in the present disclosure.

In some technical embodiments of the present disclosure, the n=2, t=1, and other variables are as defined in the present disclosure.

In some technical embodiments of the present disclosure, the n=2, t=2, and other variables are as defined in the present disclosure.

There are still some technical embodiments of the present disclosure which are obtained by free combination of the above variables.

The present disclosure provides a compound of the following formula or a pharmaceutically acceptable salt thereof,

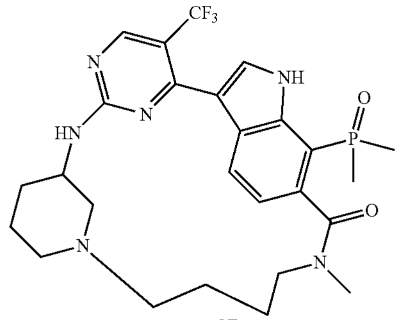

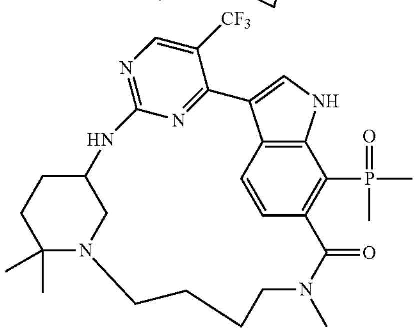

-continued
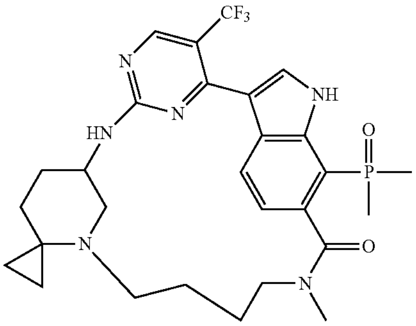
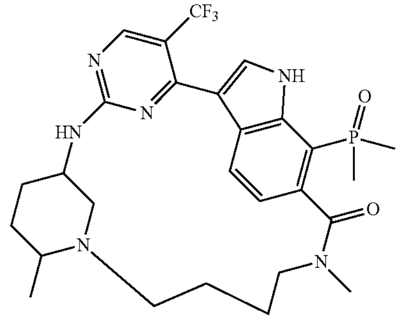
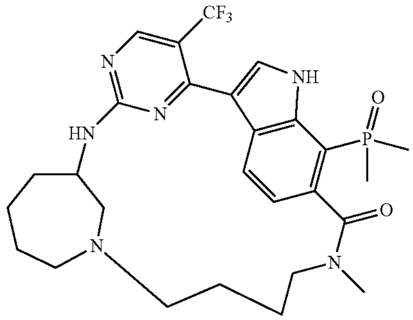
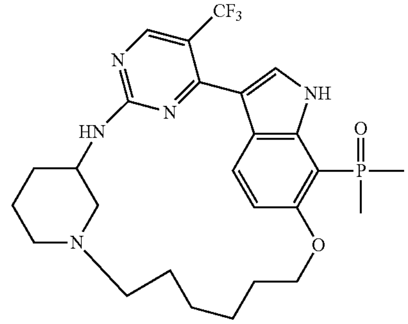
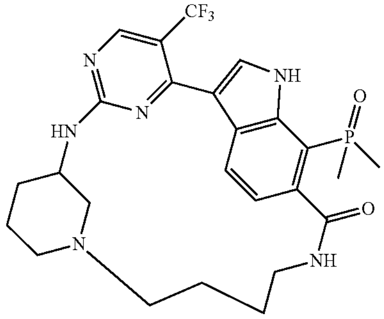
-continued
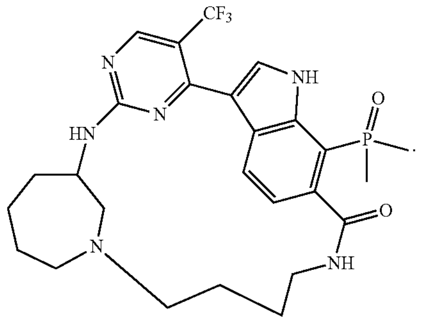
The present disclosure provides a compound of the following formula or a pharmaceutically acceptable salt thereof,
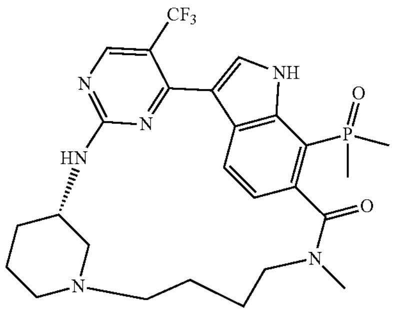
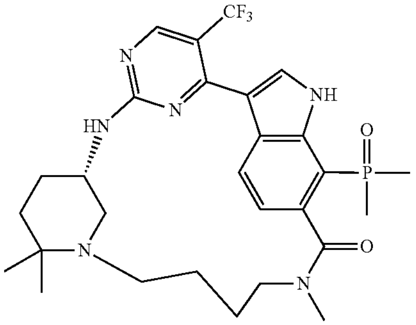
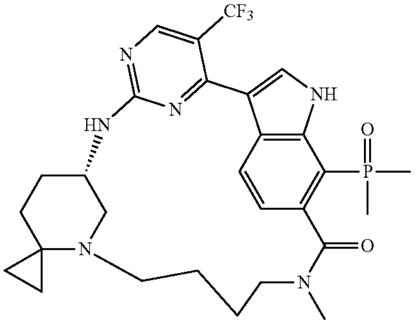

-continued
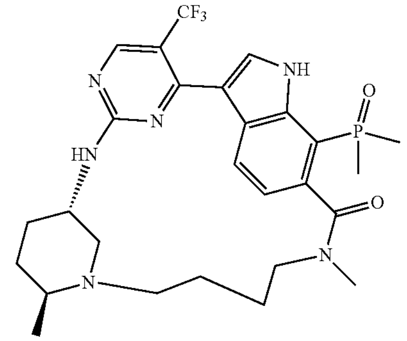
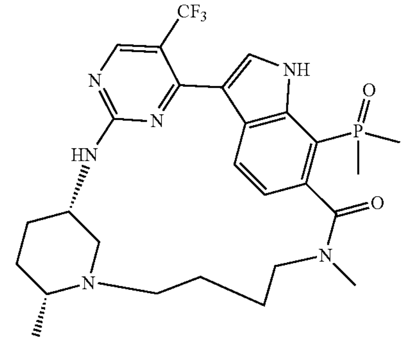
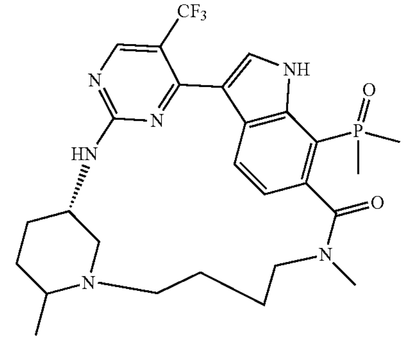
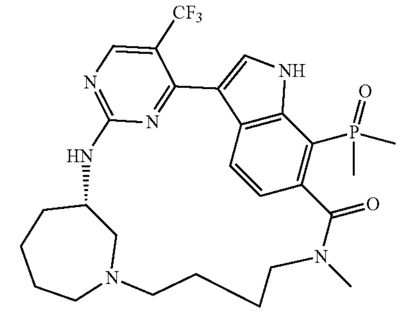
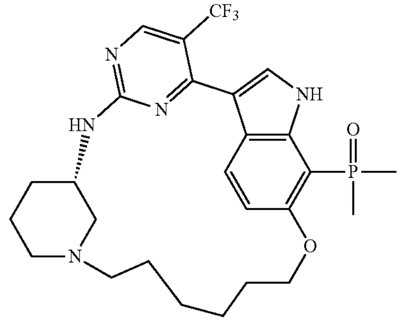
-continued
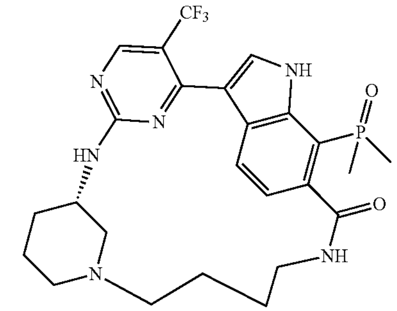
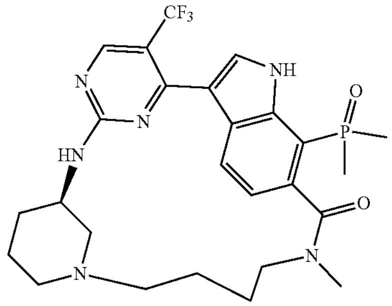
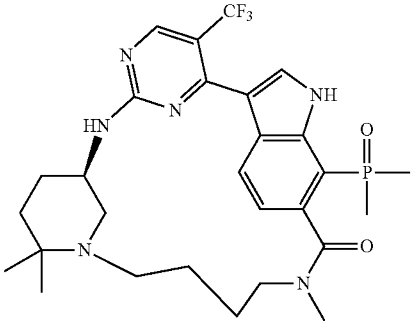
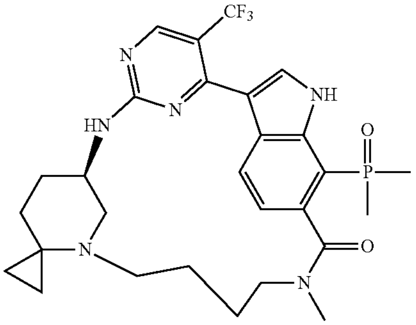
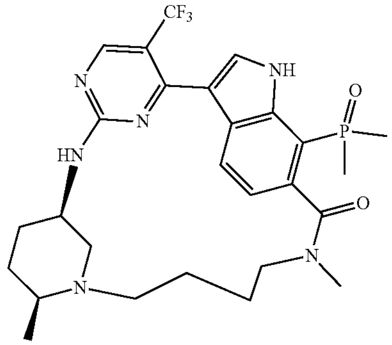

-continued

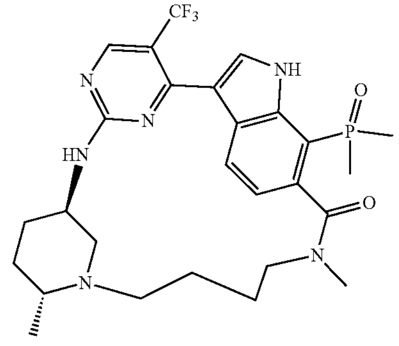

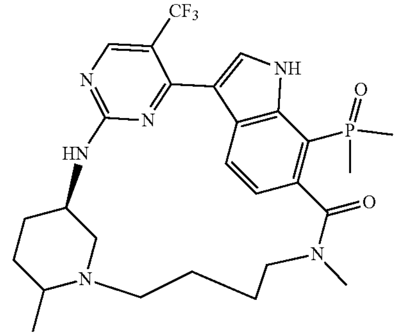

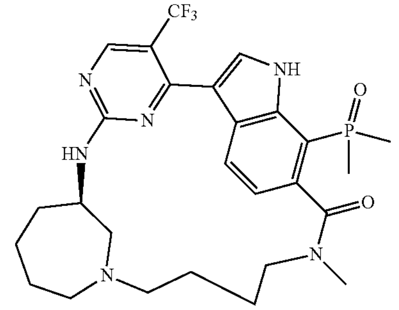

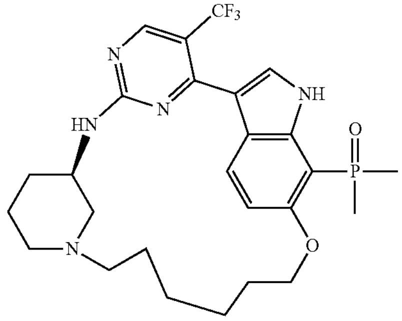

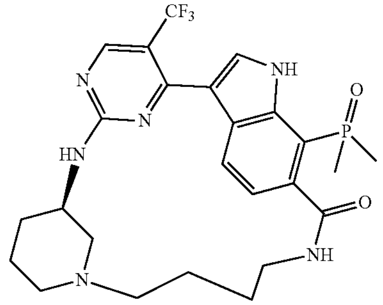

-continued

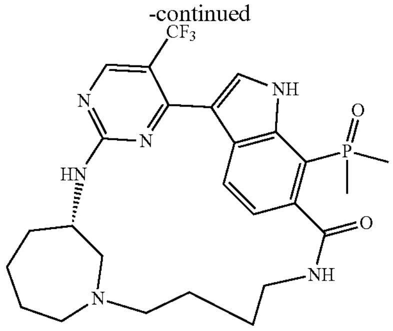

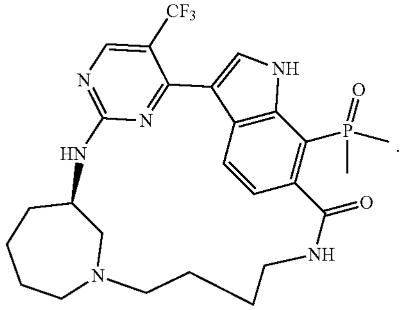 [SMILES: CP(C)(=O)c1c2ccc3c(c[nH]c13)-c1nc(ncc1C(F)(F)F)N[C@@H]1CCCCN(CCCCNC2=O)C1]

The present disclosure also provides a use of the compound or the pharmaceutically acceptable salt thereof defined in any of the above technical embodiments in the manufacture of a medicament for treating a disease related to CDK7.

In some technical embodiments of the present disclosure, the disease related to CDK7 refers to breast cancer, and other variables are as defined in the present disclosure.

A second aspect of the present disclosure also provides a pharmaceutical composition, comprising the compound or the pharmaceutically acceptable salt thereof defined in any of the above technical embodiments and a pharmaceutically acceptable carrier.

The present disclosure also provides a method for treating the disease related to CDK7 in a subject in need thereof, comprising administering to the subject an effective amount of the compound or the pharmaceutically acceptable salt thereof defined in any of the above technical embodiments, or the pharmaceutical composition.

The present disclosure also provides a use of the compound, an isomer thereof, the pharmaceutically acceptable salt thereof, or the pharmaceutical composition in the manufacture of a medicament for treating a disease related to CDK7.

In some technical embodiments of the present disclosure, the disease related to CDK7 refers to breast cancer, and other variables are as defined in the present disclosure.

Technical Effect

The compounds of the present disclosure have strong inhibitory activity against CDK7, good kinase selection, and good in vivo efficacy in triple-negative breast HCC70 model with primary resistance to CDK4/6 inhibitors, and can be used for the treatment of CDK4/6 inhibitor-resistant HR+Her2− breast cancer, triple-negative breast cancer, and other diseases.

DEFINITION AND DESCRIPTION

Unless otherwise specified, the following terms and phrases used herein are intended to have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction, or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting such compounds with a sufficient amount of base in a pure solution or a suitable inert solvent. The pharmaceutically acceptable base addition salt includes a salt of sodium, potassium, calcium, ammonium, organic amine, magnesium, or similar salts. When the compound of the present disclosure contains a relatively basic functional group, an acid addition salt can be obtained by contacting such compounds with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and salts of amino acid (such as arginine), and a salt of an organic acid such as glucuronic acid. Certain specific compounds of the present disclosure contain both basic and acidic functional groups, and thus can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, as well as racemic mixtures and other mixtures thereof, such as enantiomer or diastereomer enriched mixtures, all of which are within the scope of the present disclosure.

Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ), a wave line ( ) is used to represent a wedged solid bond ( ) or a wedged dashed bond ( ), or the wave line ( ) is used to represent a straight solid bond ( ) and a straight dashed bond ( ).

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

Optically active (R)- and (S)-isomers as well as D and L isomers can be prepared using chiral synthesis, chiral reagents, or other conventional techniques. If one kind of enantiomer of certain compound of the present disclosure is to be obtained, it can be obtained by asymmetric synthesis or derivative action of chiral auxiliary, wherein the resulting diastereomeric mixture is separated and the auxiliary group is cleaved to provide the pure desired enantiomer. Alternatively, when the molecule contains a basic functional group (such as amino) or an acidic functional group (such as carboxyl), a salt of a diastereoisomer is formed with an appropriate optically active acid or base, and then diastereomeric resolution is performed by conventional methods known in the art, and then the pure enantiomer is recovered. In addition, the enantiomer and the diastereoisomer are generally separated through chromatography which uses a chiral stationary phase and optionally combines with a chemical derivatization method (such as carbamate generated from amine).

The compound of the present disclosure may contain an unnatural proportion of atomic isotope at one or more atoms that constitute the compound. For example, the compound can be radiolabeled with a radioactive isotope, such as tritium ($^{3}H$), iodine-125 ($^{125}I$), or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

"Optional" or "optionally" means that the subsequent event or condition may occur but not requisite, and that the term includes the instance in which the event or condition occurs and the instance in which the event or condition does not occur.

The term "substituted" means that one or more hydrogen atoms on a specific atom is substituted by the substituent, including deuterium and hydrogen variables, as long as the valence of the specific atom is normal and the substituted compound is stable. When the substituent is an oxygen (i.e., =O), it means that two hydrogen atoms are substituted. Positions on an aromatic ring cannot be substituted with a ketone.

The term "optionally substituted" means that an atom can be substituted by a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent is absent. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

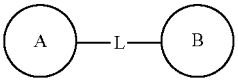

is -M-W—, then -M-W— can link ring A and ring B to form

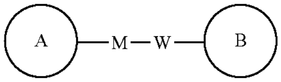

in the direction same as left-to-right reading order, and form

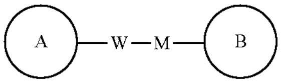

in the direction contrary to left-to-right reading order. A combination of the linking groups, substituents and/or variants thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is an H atom at the linkable site, then the number of H atoms at the site will decrease correspondingly with the number of the chemical bonds linking thereto so as to meet the corresponding valence. The chemical bond between the site and other groups can be represented by a straight solid bond (  ), a straight dashed bond (  ), or a wavy line (  ).

For example, the straight solid bond in $-OCH_3$ means that it is linked to other groups through the oxygen atom in the group; the straight dashed bond in

means that it is linked to other groups through the two ends of the nitrogen atom in the group; the wave line in

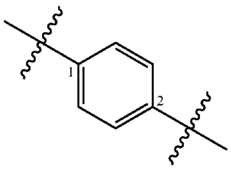 [SMILES: *c1ccc(*)cc1]

means that the phenyl group is linked to other groups through carbon atoms at position 1 and position 2;

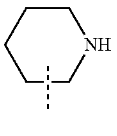

means that it can be linked to other groups through any linkable sites on the piperidinyl by one chemical bond, including at least four types of linkage, including

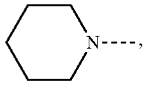, 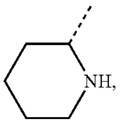, 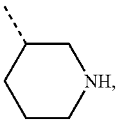, and

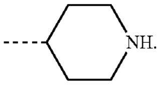.

Even though the H atom is drawn on the —N—,

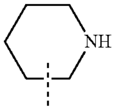

still includes the linkage of

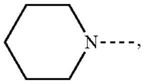, merely when one chemical bond was connected, the H of this site will be reduced by one to the corresponding monovalent piperidinyl.

Unless otherwise specified, the number of atoms in a ring is usually defined as the number of ring members, for example, "5- to 7-membered ring" refers to a "ring" in which 5 to 7 atoms are arranged around.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$, $C_{2-3}$ alkyl, etc.; it can be monovalent (such as methyl), divalent (such as methylene), or multivalent (such as methine). Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$, $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-3}$ haloalkyl" refers to monohaloalkyl and polyhaloalkyl containing 1 to 3 carbon atoms. The $C_{1-3}$ haloalkyl includes $C_{1-2}$, $C_{2-3}$, $C_3$, $C_2$, $C_1$ haloalkyl, etc. Examples of $C_{1-3}$ haloalkyl include, but are not limited to, trifluoromethyl, trichloromethyl, 2,2,2-trifluoroethyl, pentafluoroethyl, pentachloroethyl, 3-bromopropyl, etc. Unless otherwise specified, "$C_{2-4}$ alkenyl" is used to mean a linear or branched hydrocarbon group consisting of 2 to 4 carbon atoms containing at least one carbon-carbon double bond, and the carbon-carbon double bond may be located at any position of the group. The $C_{2-4}$ alkenyl includes $C_{2-3}$ alkenyl, $C_4$ alkenyl, $C_3$ alkenyl, $C_2$ alkenyl, etc.; the $C_{2-4}$ alkenyl can be monovalent, divalent, or multivalent. Examples of $C_{2-4}$ alkenyl include, but are not limited to, vinyl, propenyl, butenyl, butadienyl, etc. Unless otherwise specified, "$C_{2-3}$ alkenyl" is used to mean a linear or branched hydrocarbon group consisting of 2 to 3 carbon atoms containing at least one carbon-carbon double bond, and the carbon-carbon double bond may be located at any position of the group. The $C_{2-3}$ alkenyl includes $C_3$ alkenyl and $C_2$ alkenyl; the $C_{2-3}$ alkenyl can be monovalent, divalent, or multivalent. Examples of $C_{2-3}$ alkenyl include, but are not limited to, vinyl, propenyl, etc.

Unless otherwise specified, the term "halogen element" or "halogen" by itself or as part of another substituent refers to a fluorine, chlorine, bromine, or iodine atom.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc.; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, 6- to 10-membered ring, etc.

Unless otherwise specified, the term "4- to 6-membered heterocycloalkyl" by itself or in combination with other terms refers to a saturated cyclic group consisting of 4 to 6 ring atoms, wherein 1, 2, 3, or 4 ring atoms are heteroatoms independently selected from O, S, and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic system includes a spiro ring, a fused ring, and a bridged ring. In addition, with regard to the "4- to 6-membered heterocycloalkyl", a heteroatom may occupy the connection position of the heterocycloalkyl with the rest of the molecule. The 4- to 6-membered heterocycloalkyl includes 5- to 6-membered, 4-membered, 5-membered, 6-membered heterocycloalkyl, etc. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl, tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxinyl, dithianyl, isoxazolidinyl, isothiazolidinyl, 1,2-oxazinyl, 1,2-thiazinyl, hexahydropyridazinyl, etc.

Unless otherwise specified, "$C_{3-6}$ cycloalkyl" refers to a saturated cyclic hydrocarbon group consisting of 3 to 6 carbon atoms, which can be monocyclic and bicyclic, and the $C_{3-6}$ cycloalkyl includes $C_{3-5}$, $C_{4-5}$, $C_{5-6}$ cycloalkyl, etc.; it can be monovalent, divalent, or multivalent. Examples of $C_{3-6}$ cycloalkyl include, but are not limited to, cyclopropyl, cyclobutyl, cyclopentyl, cyclohexyl, etc.

Unless otherwise specified, the term "3- to 6-membered heterocycloalkyl" by itself or in combination with other terms refers to a saturated cyclic group consisting of 3 to 6 ring atoms, wherein 1, 2, 3, or 4 ring atoms are heteroatoms independently selected from O, S, and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic system includes a spiro ring, a fused ring, and a bridged ring. In addition, with regard to the "3- to 6-membered heterocycloalkyl", a heteroatom may occupy the connection position of the heterocycloalkyl with the rest of the molecule. The 3- to 6-membered heterocycloalkyl includes 4- to 6-membered, 5- to 6-membered, 4-membered, 5-membered, 6-membered heterocycloalkyl, etc. Examples of 3- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl, tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxinyl, dithianyl, isoxazolidinyl, isothiazolidinyl, 1,2-oxazinyl, 1,2-thiazinyl, hexahydropyridazinyl, etc.

The term "leaving group" refers to a functional group or atom which can be replaced by another functional group or atom through a substitution reaction (such as nucleophilic substitution reaction). For example, representative leaving groups include triflate; chlorine, bromine, and iodine; sulfonate group, such as mesylate, tosylate, p-bromobenzenesulfonate, and p-toluenesulfonate; acyloxy, such as acetoxy and trifluoroacetoxy.

The term "protecting group" includes, but is not limited to, "amino protecting group", "hydroxyl protecting group", or "mercapto protecting group". The term "amino protecting group" refers to a protecting group suitable for preventing the side reaction occurring at the nitrogen of an amino group. Representative amino protecting groups include, but are not limited to: formyl; acyl, such as alkanoyl (e.g., acetyl, trichloroacetyl, or trifluoroacetyl); alkoxycarbonyl, such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), trityl (Tr), and 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing the side reaction on a hydroxyl group. Representative hydroxyl protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyldimethylsilyl (TBS).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, and preferred embodiments include, but are not limited to, the examples of the present disclosure.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), diffraction intensity data are collected from the cultured single crystal using a Bruker D8 venture diffractometer with CuKα radiation as the light source and scanning mode: φ/ω scan, and after collecting the relevant data, the crystal structure is further analyzed by direct method (Shelxs97), so that the absolute configuration can be confirmed.

The solvents used in the present disclosure are commercially available. The following abbreviations are used in the present disclosure: $NH_4HCO_3$ represents ammonium bicarbonate, Xantphos Pd G4 represents methanesulfonato[9,9-dimethyl-4,5-bis(diphenylphosphino)xanthene](2-methylamino-1,1-biphenyl-2-yl)palladium(II).

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

The present disclosure is described in detail by the examples below, but it does not mean that there are any adverse restrictions on the present disclosure. The present disclosure has been described in detail herein, and its specific embodiments have also been disclosed; for those skilled in the art, it is obvious to make various modifications and improvements to the specific embodiments of the present disclosure without departing from the spirit and scope of the present disclosure.

Example 1

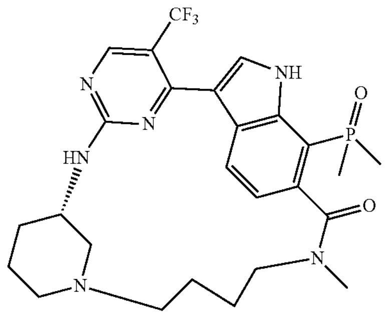

1

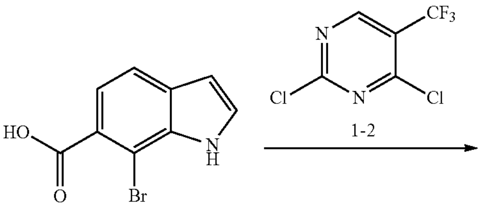

1-1

1-2

-continued

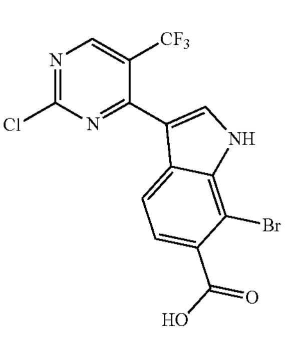

1-3

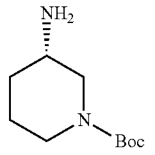

1-4

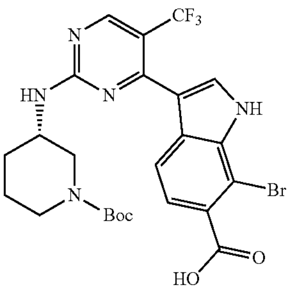

1-5

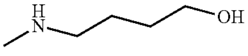

1-6

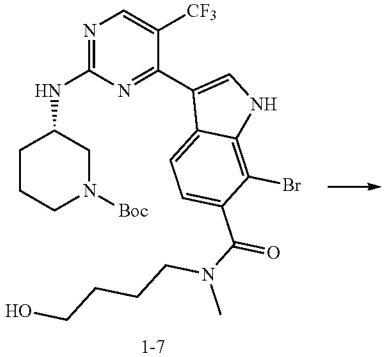

1-7

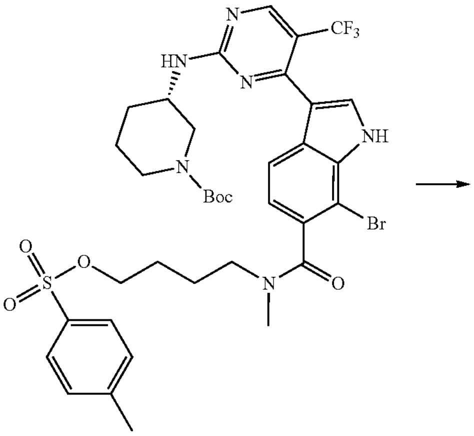

1-8

-continued

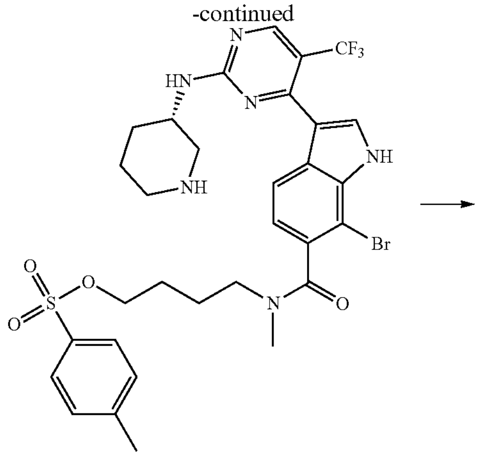

1-9

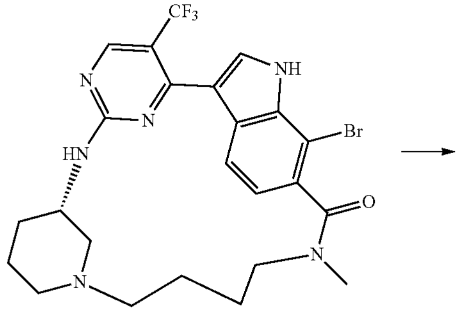

1-10

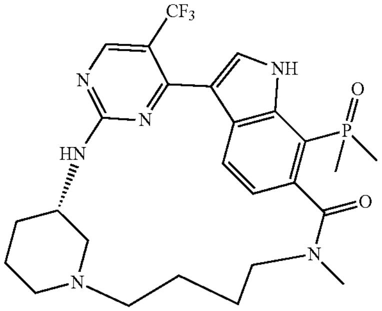

1

Step 1:

Trifluoromethanesulfonic acid (3.63 g) was added to a hexafluoroisopropanol solvent (60 mL) of compound 1-1 (5.8 g) and compound 1-2 (5.77 g) at 25° C., and the mixture was heated to 65° C. and reacted for 16 hours. The reaction mixture was added with 50 mL of water and then extracted with ethyl acetate (50 mL*3). The combined organic phases were washed once with brine (100 mL), dried over anhydrous sodium sulfate, filtered, and the filtrate was concentrated to obtain a residue. The residue was purified by column chromatography (silica gel, eluent, petroleum ether: ethyl acetate=100:1 to 1:1) to obtain compound 1-3. LCMS (ESI) m/z: 420.0, 422.0 (M+1).

Step 2:

Diisopropylethylamine (3.96 g) was added to a mixture of compound 1-3 (4.3 g) and compound 1-4 (3.07 g) in 1-methyl-2-pyrrolidone (50 mL) at 25° C., and the mixture was stirred at 65° C. for 5 hours. After the reaction was completed, the reaction mixture was added with water (50 mL) and then extracted with ethyl acetate (100 mL*3). The aqueous phase was added with dilute hydrochloric acid (1 M) to adjust the pH to 4 and then extracted with ethyl acetate (100 mL*3). The combined organic phases were washed with saturated brine (200 mL), dried over anhydrous sodium sulfate, filtered, and the filtrate was concentrated to obtain compound 1-5. LCMS (ESI) m/z: 584.1, 586.1 (M+1).

Step 3:

Triethylamine (519.47 mg) and o-(7-azabenzotriazole-1-yl)-N,N,N,N-tetramethyluronium hexafluorophosphate (1.30 g) were added to a solution of compound 1-5 (1 g) and compound 1-6 (264.80 mg) in N,N-dimethylformamide (2 mL) at 25° C., and the mixture was stirred at 25° C. for 4 hours. After the reaction was completed, the reaction mixture was added with water (20 mL) and then extracted with ethyl acetate (20 mL*3). The combined organic phases were washed with saturated brine (50 mL), dried over anhydrous sodium sulfate, filtered, and the filtrate was concentrated to obtain a residue. The residue was purified by column chromatography (silica gel, eluent, petroleum ether:ethyl acetate=100:1 to 0:1) to obtain compound 1-7. LCMS (ESI) m/z: 669.2, 671.2 (M+1).

$^1$H NMR (400 MHz, DMSO-d6) δ ppm 11.98-12.31 (m, 1 H) 8.58-8.71 (m, 1 H) 7.91-8.01 (m, 1 H) 7.76-7.89 (m, 1 H) 6.94-7.09 (m, 1 H) 5.68-5.83 (m, 1 H) 4.21-4.60 (m, 1 H) 3.74-3.97 (m, 2 H) 3.43-3.53 (m, 2 H) 3.21-3.28 (m, 1 H) 3.06-3.19 (m, 1 H) 2.96-3.05 (m, 2 H) 2.72-2.80 (m, 2 H) 2.51-2.55 (m, 4 H) 1.93-1.99 (m, 1 H) 1.74-1.88 (m, 1 H) 1.65-1.71 (m, 1 H) 1.47-1.58 (m, 3 H) 1.24 (br s, 9 H).

Step 4:

p-Toluenesulfonyl chloride (149.11 mg), 4-dimethylaminopyridine (4.78 mg), and triethylamine (158.29 mg) were added to a solution of compound 1-7 (630 mg) in dichloromethane (5 mL) at 25° C., and the mixture was stirred at 25° C. under nitrogen atmosphere for 12 hours. After the reaction was completed, the reaction mixture was added with water (20 mL) and then extracted with ethyl acetate (20 mL*3). The combined organic phases were washed with saturated brine (50 mL), dried over anhydrous sodium sulfate, filtered, and the filtrate was concentrated to obtain a residue. The residue was purified by column chromatography (silica gel, eluent, petroleum ether:ethyl acetate=100:1 to 1:1) to obtain compound 1-8. LCMS (ESI) m/z: 823.2, 825.2 (M+1).

Step 5:

Trifluoroacetic acid (2.61 g) was added to a solution of compound 1-8 (300 mg) in dichloromethane (6 mL) at 25° C., and the mixture was stirred at 25° C. under nitrogen atmosphere for 6 hours. After the reaction was completed, the reaction mixture was concentrated to obtain the trifluoroacetate of compound 1-9. LCMS (ESI) m/z: 723.2, 725.2 (M+1).

Step 6:

Potassium carbonate (171.90 mg) was added to a solution of the trifluoroacetate of compound 1-9 (300 mg) in acetonitrile (20 mL) at 25° C., and the mixture was stirred at 80° C. under nitrogen atmosphere for 12 hours. After the reaction was completed, the reaction mixture was added with water (20 mL) and then extracted with ethyl acetate (20 mL*3). The combined organic phases were washed with saturated brine (50 mL), dried over anhydrous sodium sulfate, filtered, and the filtrate was concentrated to obtain a residue. The residue was purified by column chromatography (silica gel, eluent, petroleum ether:ethyl acetate=100:1 to 0:1) to obtain compound 1-10. LCMS (ESI) m/z: 551.2, 553.2 (M+1).

Step 7:

Dimethylphosphine oxide (9.46 mg), Xantphos Pd G4 (17.50 mg), and potassium phosphate (25.736 mg) were added to a solution of compound 1-10 (35 mg) in dioxane (2 mL) at 25° C., and the mixture was stirred at 120° C. under nitrogen atmosphere for 12 hours. The reaction mixture was added with water (50 mL) and then extracted with ethyl acetate (50 mL*3). The combined organic phases were washed with saturated brine (50 mL), dried over anhydrous sodium sulfate, filtered, and concentrated to obtain a residue. The residue was purified by preparative HPLC (column model: Phenomenex C18 75*30 mm*3 μm; mobile phase: [water (formic acid)-acetonitrile]:acetonitrile %: 8% to 38%, 7 min) to obtain the formate of compound 1. LCMS (ESI) m/z: 549.2 (M+1); $^1$H NMR (400 MHz, DMSO-d6) δ ppm 12.00 (br s, 1 H) 8.76-8.95 (m, 1 H) 8.52-8.60 (m, 1 H) 8.06 (br s, 1 H) 7.66-7.79 (m, 1 H) 7.07-7.21 (m, 1 H) 3.72-3.96 (m, 1 H) 3.45-3.54 (m, 1 H) 2.98 (s, 3 H) 2.67-2.81 (m, 2 H) 2.54-2.64 (m, 1 H) 1.83-2.08 (m, 7 H) 1.59-1.77 (m, 8 H) 1.31-1.55 (m, 4 H).

Example 2

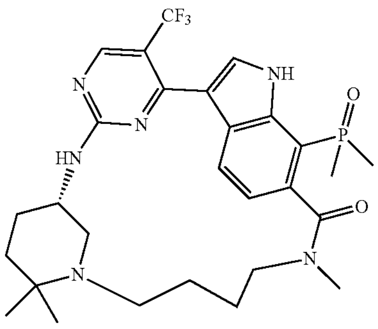

2

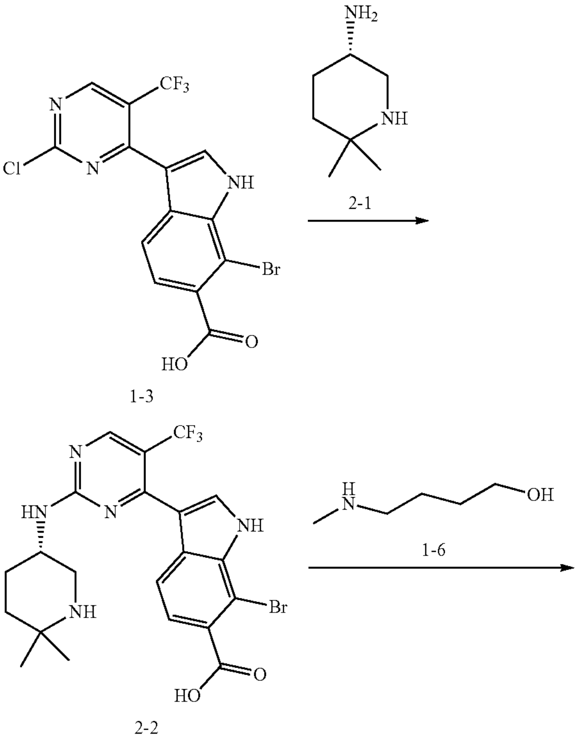

2-1

1-3

1-6

2-2

-continued

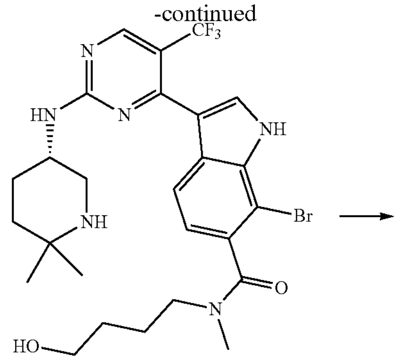

2-4

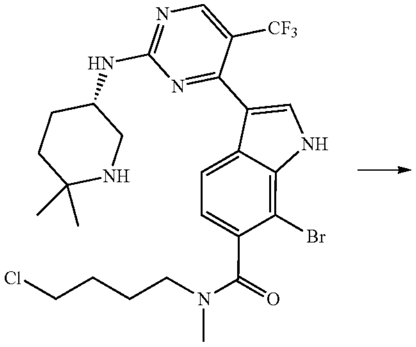

2-5

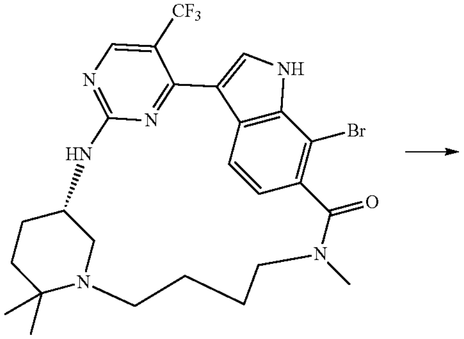

2-6

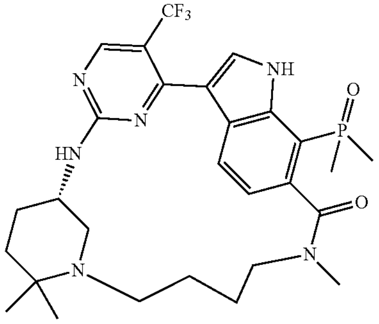

2

Step 1:

Diisopropylethylamine (2.90 g) was added to a mixture of compound 1-3 (2.2 g) and compound 2-1 (888.26 mg, hydrochloride) in 1-methyl-2-pyrrolidone (25 mL) at 25° C., and the mixture was stirred at 65° C. for 12 hours. After the reaction was completed, the reaction mixture was added with water (20 mL) and then extracted with ethyl acetate (30 mL*3). The combined organic phases were washed twice with saturated brine (20 mL), dried over anhydrous sodium sulfate, filtered, and concentrated to obtain compound 2-2. LCMS (ESI) m/z: 512.1, 514.1 (M+1).

Step 2:

Diisopropylethylamine (782.03 mg) and o-(7-azabenzo-triazole-1-yl)-N,N,N,N-tetramethyluronium hexafluoro-phosphate (920.29 mg) were added to a solution of compound 2-2 (620 mg) and compound 1-6 (187.27 mg) in N,N-dimethylformamide (2 mL) at 25° C., and the mixture was stirred at 25° C. for 12 hours. After the reaction was completed, the reaction mixture was added with water (20 mL) and then extracted with ethyl acetate (50 mL*3). The combined organic phases were washed with saturated brine (50 mL*2), dried over anhydrous sodium sulfate, filtered, and the filtrate was concentrated to obtain a residue. The residue was purified by column chromatography (silica gel, eluent, dichloromethane:methanol=100:1 to 10:1) to obtain compound 2-4. LCMS (ESI) m/z: 597.2, 599.2 (M+1).

Step 3:

Thionyl chloride (154.81 mg) and pyridine (102.93 mg) were added to a solution of compound 2-4 (500 mg) in dichloromethane (5 mL) at 25° C., and the mixture was stirred at 50° C. under nitrogen atmosphere for 2 hours. After the reaction was completed, the reaction mixture was added with water (20 mL) and then extracted with ethyl acetate (50 mL*2). The combined organic phases were washed with saturated brine (50 mL*2), dried over anhydrous sodium sulfate, filtered, and the filtrate was concentrated to obtain a residue. The residue was purified by preparative HPLC (column model: Phenomenex luna C18 150*40 mm*15 μm; mobile phase: [water (formic acid)-acetonitrile]:acetonitrile %: 18% to 48%, 10 min) to obtain compound 2-5. LCMS (ESI) m/z: 615.0, 617.0 (M+1).

Step 4:

Potassium carbonate (136.06 mg) and sodium iodide (47.74 mg) were added to a solution of compound 2-5 (200 mg) in acetonitrile (10 mL) at 25° C., and the mixture was stirred at 85° C. under nitrogen atmosphere for 24 hours. After the reaction was completed, the reaction mixture was added with water (10 mL) and then extracted with ethyl acetate (20 mL*3). The combined organic phases were washed with saturated brine (20 mL*2), dried over anhydrous sodium sulfate, filtered, and concentrated to obtain a residue. The residue was purified by column chromatography (silica gel, eluent, dichloromethane:methanol=100:1 to 10:1) to obtain compound 2-6. LCMS (ESI) m/z: 579.1, 581.1 (M+1).

Step 5:

Dimethylphosphine oxide (4.91 mg), Xantphos Pd G4 (9.09 mg), and potassium phosphate (13.366 mg) were added to a solution of compound 2-6 (20 mg) in dioxane (1 mL) at 25° C., and the mixture was stirred at 120° C. under nitrogen atmosphere for 12 hours. The reaction mixture was added with water (20 mL) and then extracted with ethyl acetate (30 mL*3). The combined organic phases were washed twice with saturated brine (30 mL*2), dried over anhydrous sodium sulfate, filtered, and concentrated to obtain a residue. The residue was purified by preparative HPLC (column model: Phenomenex C18 75*30 mm*3 μm; mobile phase: [water (formic acid)-acetonitrile]:acetonitrile %: 5% to 35%, 7 min) to obtain the formate of compound 2. LCMS (ESI) m/z: 577.3 (M+1). $^1H$ NMR (400 MHz, $CD_3OD$) δ ppm 8.93-9.17 (m, 1 H) 8.48-8.58 (m, 1 H) 8.05-8.21 (m, 1 H) 7.72-7.97 (m, 1 H) 7.22-7.32 (m, 1 H) 4.00-4.22 (m, 1 H) 3.11 (s, 4 H) 2.84-2.97 (m, 1 H) 2.56-2.73

(m, 1 H) 2.36-2.55 (m, 1 H) 1.94-2.07 (m, 6 H) 1.78-1.86 (m, 6 H) 1.58-1.72 (m, 3 H) 1.17-1.33 (m, 7 H).

Example 3

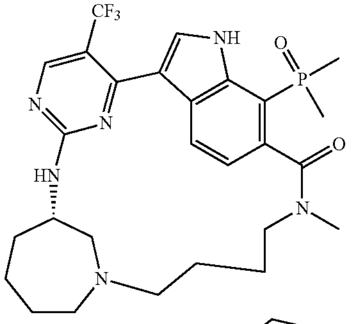

3

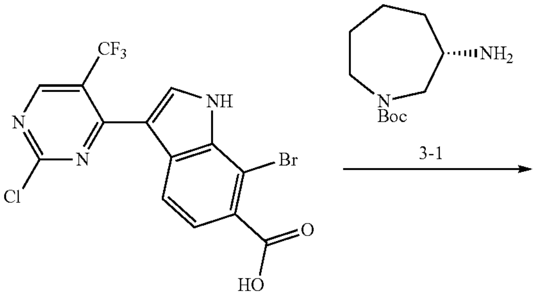

1-3

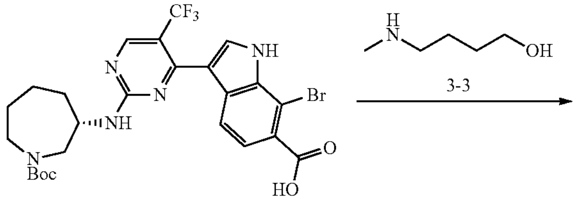

3-2

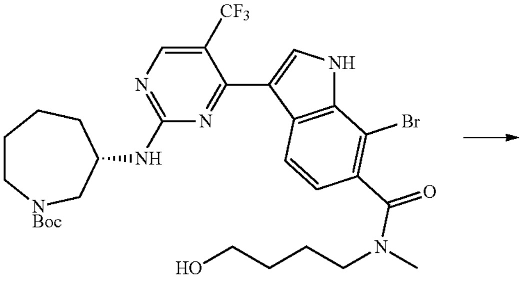

3-4

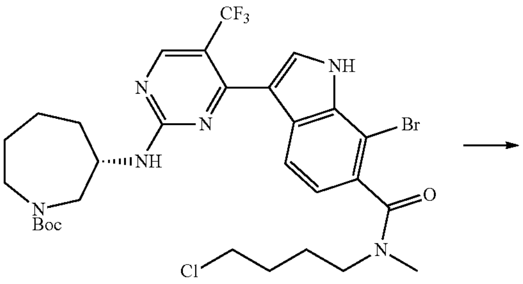

3-5

-continued

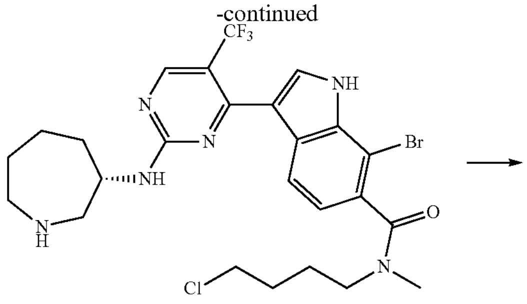

3-6

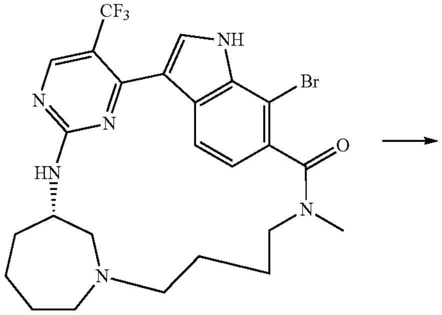

3-7

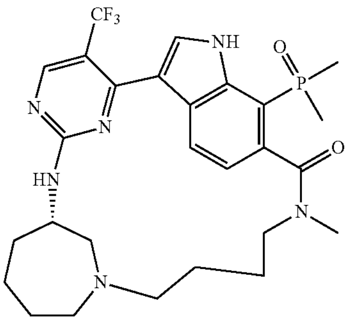

3

Step 1:

Compound 3-1 (1.53 g) and diisopropylethylamine (1.84 g) were added to a solution of compound 1-3 (2 g) in N-methylpyrrolidone (20 mL) at room temperature, and the mixture was reacted at 45° C. for 12 hours. The reaction mixture was diluted with water (50 mL) and extracted with ethyl acetate (30 mL*2). The combined organic phases were washed with saturated brine (60 mL), dried over anhydrous sodium sulfate, filtered, and concentrated under reduced pressure to obtain the crude product compound 3-2. LCMS (ESI) m/z: 598.1, 600.1 (M+1).

Step 2:

Compound 3-3 (775.77 mg), o-(7-azabenzotriazole-1-yl)-N,N,N,N-tetramethyluronium hexafluorophosphate (3.81 g), and diisopropylethylamine (3.24 g) were added to a solution of compound 3-2 (3 g) in N,N-dimethylformamide (40 mL) at room temperature, and the mixture was reacted at 25° C. for 1 hour. The reaction mixture was first diluted with water (100 mL), extracted with ethyl acetate (100 mL), and then the organic phase was washed with saturated brine (100 mL), dried over anhydrous sodium sulfate, filtered, and concentrated under reduced pressure to obtain a crude product, which was purified by column chromatography (petroleum ether/ethyl acetate=1/0 to 0/1) to obtain compound 3-4. LCMS (ESI) m/z: 683.1, 685.1 (M+1).

Step 3:

Pyridine (115.72 mg) and thionyl chloride (174.05 mg) were added to a solution of compound 3-4 (0.5 g) in tetrahydrofuran (10 mL) at room temperature, and the mixture was reacted at 65° C. for 1 hour. The reaction mixture was first diluted with saturated sodium bicarbonate (20 mL) and extracted with ethyl acetate (20 mL*2). The combined organic phases were washed with saturated brine (40 mL), dried over anhydrous sodium sulfate, filtered, and concentrated under reduced pressure to obtain a crude product, which was purified by column chromatography (petroleum ether/ethyl acetate=1/0 to 1/1) to obtain compound 3-5. LCMS (ESI) m/z: 601.2, 603.2 (M-100+1).

Step 4:

Hydrochloric acid/ethyl acetate (1.98 mL) was added to a solution of compound 3-5 (233 mg) in ethyl acetate (4 mL) at room temperature, and the mixture was reacted at 25° C. for 0.5 hours. The reaction mixture was concentrated under reduced pressure to obtain a crude product, the hydrochloride of compound 3-6.

Step 5:

Potassium carbonate (267.52 mg) and sodium iodide (58.02 mg) were added to a solution of the hydrochloride of compound 3-6 (233 mg) in acetonitrile (10 mL) at room temperature, and the mixture was reacted at 100° C. for 40 hours. The reaction mixture was filtered and concentrated under reduced pressure to obtain a crude product, which was purified by column chromatography (ethyl acetate/methanol=1/0 to 10/1) to obtain compound 3-7. LCMS (ESI) m/z: 565.2, 567.2 (M+1).

Step 6:

Potassium phosphate (360.40 mg) and methanesulfonato [9,9-dimethyl-4,5-bis(diphenylphosphino)xanthene](2-methylamino-1,1-biphenyl-2-yl)palladium(II) (272.32 mg) were added to a solution of compound 3-7 (160 mg) and dimethylphosphine oxide (441.72 mg) in 1,4-dioxane (3 mL) at room temperature, and the reaction mixture was replaced with nitrogen three times and reacted at 120° C. for 12 hours. The reaction mixture was filtered, concentrated under reduced pressure, and purified by reversed phase HPLC (column model: Phenomenex C18 75*30 mm*3 μm; mobile phase: [water (formic acid)-acetonitrile]; B %: 8% to 38%, 7 min) and normal phase HPLC (column model: Welch Ultimate XB-SiOH 250*50*10 μm; mobile phase: [n-hexane-ethanol]; B %: 1% to 40%, 15 min) to obtain compound 3. LCMS (ESI) m/z: 563.3 (M+1). $^1$H NMR (400 MHz, $CDCl_3$): δ=11.83 (br s, 1 H), 8.87 (br s, 1 H), 8.51 (br s, 1 H), 7.99 (br s, 1 H), 7.25-7.08 (m, 1 H), 5.23 (br d, J=8.0 Hz, 1 H), 3.48-3.37 (m, 1 H), 3.08 (s, 3 H), 2.90-2.81 (m, 1 H), 2.78-2.65 (m, 1 H), 2.49-2.18 (m, 4 H), 2.16-2.01 (m, 4 H), 1.88-1.61 (m, 14 H).

Example 4

4

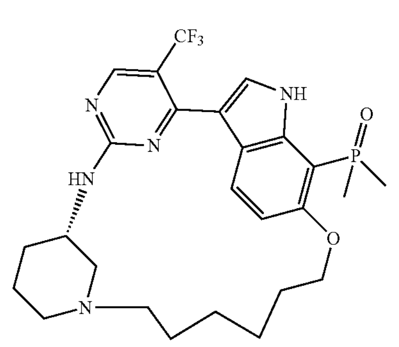

-continued

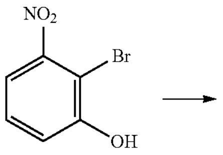

4-1

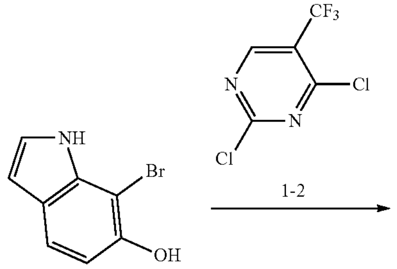

4-2

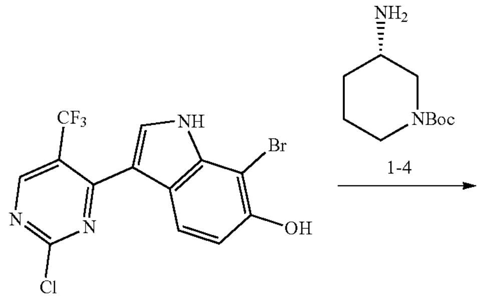

4-3

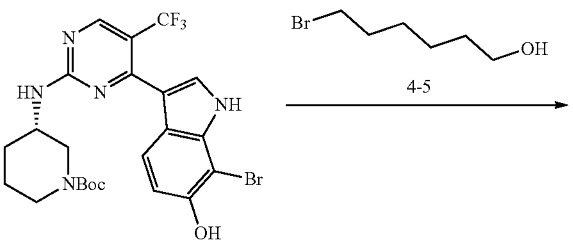

4-4

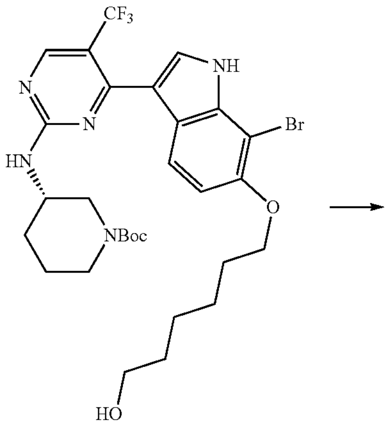

4-6

-continued

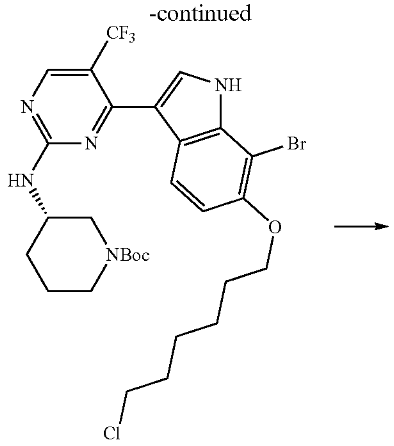

4-7

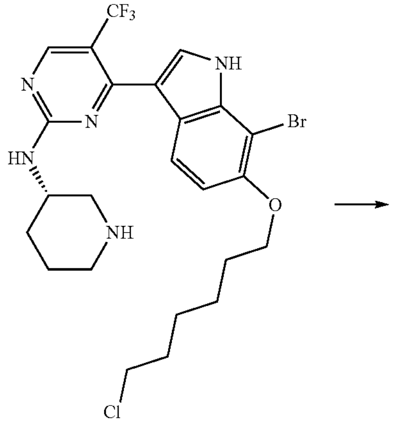

4-8

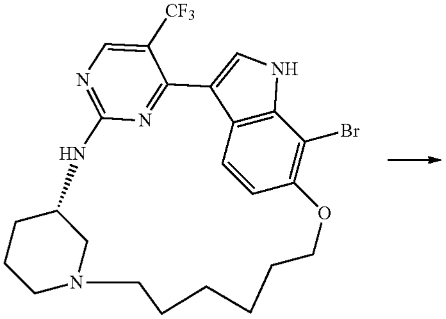

4-9

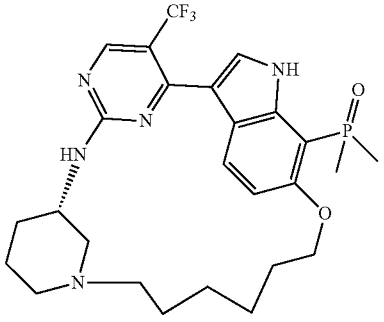

4

Step 1:

Vinylmagnesium bromide (1 M, 110.09 mL) was added dropwise to a solution of compound 4-1 (6 g) in tetrahydrofuran (60 mL) at −40° C., and the mixture was stirred at −40° C. for 2 hours. The mixture was stirred at −40° C. for another hour. After the reaction was completed, the reaction mixture was poured into saturated ammonium chloride aqueous solution (100 mL) and then extracted twice with ethyl acetate (50 mL*2). The combined organic phases were washed with saturated brine (50 mL), dried over anhydrous sodium sulfate, filtered, and concentrated to obtain a residue. The residue was purified by column chromatography (silica gel, eluent, petroleum ether:ethyl acetate=20:1 to 20:1) to obtain compound 4-2. LCMS (ESI) m/z: 210.0, 212.0 (M+1). $^1$H NMR (400 MHz, DMSO-d6) δ ppm 10.85 (br s, 1 H) 9.60 (s, 1 H) 7.32 (d, J=8.31 Hz, 1 H) 7.15 (t, J=2.69 Hz, 1 H) 6.73 (d, J=8.31 Hz, 1 H) 6.41 (dd, J=2.87, 2.14 Hz, 1 H).

Step 2:

Trifluoromethanesulfonic acid (1.67 mL) was added to a solution of compound 4-2 (4 g) and compound 1-2 (4.91 g) in hexafluoroisopropanol (40 mL) at 20° C., and the mixture was stirred at 65° C. for 12 hours. LCMS detected that the reaction was complete. After the reaction was completed, the reaction mixture was concentrated to obtain a residue, added with water (50 mL), and then extracted twice with ethyl acetate (50 mL*2). The combined organic phases were washed with saturated brine (50 mL), dried over anhydrous sodium sulfate, filtered, and concentrated to obtain a residue. The residue was purified by column chromatography (silica gel, eluent, petroleum ether:ethyl acetate=20:1 to 10:1) to obtain compound 4-3. LCMS (ESI) m/z: 391.8, 393.8 (M+1).

Step 3:

Diisopropylethylamine (2.39 g) was added to a solution of compound 4-3 (2.42 g) and compound 1-4 (1.85 g) in N-methylpyrrolidone (30 mL) at 20° C., and the mixture was stirred at 50° C. for 12 hours. After the reaction was completed, the reaction mixture was poured into water (50 mL) and then extracted twice with ethyl acetate (50 mL*2). The combined organic phases were washed with water (50 mL) and saturated brine (50 mL), dried over anhydrous sodium sulfate, filtered, and concentrated to obtain a residue. The residue was purified by column chromatography (silica gel, eluent, petroleum ether:ethyl acetate=5:1 to 3:1) to obtain compound 4-4. LCMS (ESI) m/z: 556.0, 558.0 (M+1).

Step 4:

Potassium carbonate (1.68 g) was added to a solution of compound 4-4 (2.25 g) and compound 4-5 (732.26 mg) in N,N-dimethylformamide (20 mL) at 20° C., and the mixture was stirred at 60° C. for 3 hours. After the reaction was completed, the reaction mixture was poured into water (50 mL) and then extracted twice with ethyl acetate (50 mL*2). The combined organic phases were washed with water (50 mL) and saturated brine (50 mL), dried over anhydrous sodium sulfate, filtered, and concentrated to obtain a residue. The residue was purified by column chromatography (silica gel, eluent, petroleum ether:ethyl acetate=5:1 to 2:1) to obtain compound 4-6. LCMS (ESI) m/z: 656.2, 658.2 (M+1).

Step 5:

Pyridine (307.23 mg) and thionyl chloride (462.09 mg) were added to a solution of compound 4-6 (1.7 g) in tetrahydrofuran (20 mL) at 20° C., and the mixture was stirred at 65° C. for 1 hour. After the reaction was completed, the reaction mixture was poured into water (30 mL) and then extracted twice with ethyl acetate (30 mL*2). The combined organic phases were washed with saturated brine (30 mL), dried over anhydrous sodium sulfate, filtered, and concentrated to obtain a residue. The residue was purified by column chromatography (silica gel, eluent, petroleum ether: ethyl acetate=5:1 to 5:1) to obtain compound 4-7. LCMS (ESI) m/z, 674.2, 676.2 (M+1).

Step 6:

Hydrochloric acid/methanol (4 M, 10 mL) was added to a solution of compound 4-7 (1.2 g) in methanol (10 mL) at 20° C., and the mixture was stirred at 20° C. for 1 hour. After the reaction was completed, the reaction mixture was concentrated to obtain the hydrochloride of compound 4-8. LCMS (ESI) m/z, 574.1, 576.1 (M+1).

Step 7:

Potassium carbonate (1.13 g) and potassium iodide (271.54 mg) were added to a solution of the hydrochloride of compound 4-8 (1 g) in acetonitrile (20 mL) at 20° C., and the mixture was stirred at 100° C. for 16 hours. The mixture was stirred at 100° C. for another 24 hours. After the reaction was completed, the reaction mixture was filtered, the filter cake was washed with ethyl acetate (50 mL), and the filtrate was concentrated to obtain a residue. The residue was purified by preparative HPLC (column model: Phenomenex luna C18 150*40 mm*15 μm; mobile phase: [water (formic acid)-acetonitrile]: 13% to 43%, 10 min) to obtain the formate of compound 4-9. LCMS (ESI) m/z: 538.0 (M+1).

Step 8:

Methanesulfonato[9,9-dimethyl-4,5-bis(diphenylphosphino)xanthene](2-methylamino-1,1-biphenyl-2-yl)palladium(II) (214.50 mg) and potassium phosphate (141.93 mg) were added to a solution of the formate of compound 4-9 (120 mg) and dimethylphosphine oxide (521.88 mg) in 1,4-dioxane (10 mL) at 20° C., and the mixture was stirred at 120° C. under nitrogen atmosphere for 24 hours. After the reaction was completed, the reaction mixture was filtered, the filter cake was washed with ethyl acetate (20 mL), and the filtrate was concentrated to obtain a residue. The residue was purified by preparative HPLC (column model: Waters Xbridge C18 150*50 mm*10 μm; mobile phase: [water ($NH_4HCO_3$)-acetonitrile]: 52% to 82%, 10 min) to obtain compound 4. LCMS (ESI) m/z: 536.2 (M+1). $^1H$ NMR (400 MHz, $CD_3OD$) δ ppm 8.50 (s, 1 H) 8.27 (d, J=8.88 Hz, 1 H) 7.70 (s, 1 H) 7.12 (dd, J=9.07, 4.82 Hz, 1 H) 4.59 (dq, J=8.79, 6.37 Hz, 2 H) 4.30-4.42 (m, 1 H) 3.72-3.89 (m, 2 H) 2.96 (br d, J=11.26 Hz, 1 H) 2.49-2.65 (m, 1 H) 2.18-2.32 (m, 1 H) 1.97-2.07 (m, 1 H) 1.89 (dd, J=18.14, 14.13 Hz, 7 H) 1.58-1.80 (m, 5 H) 1.28-1.48 (m, 6 H).

Example 5

5

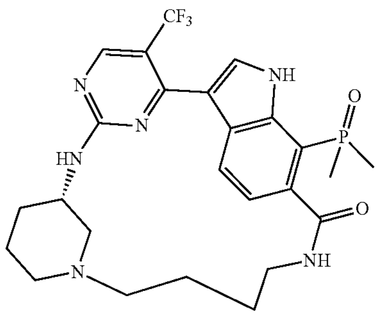

-continued

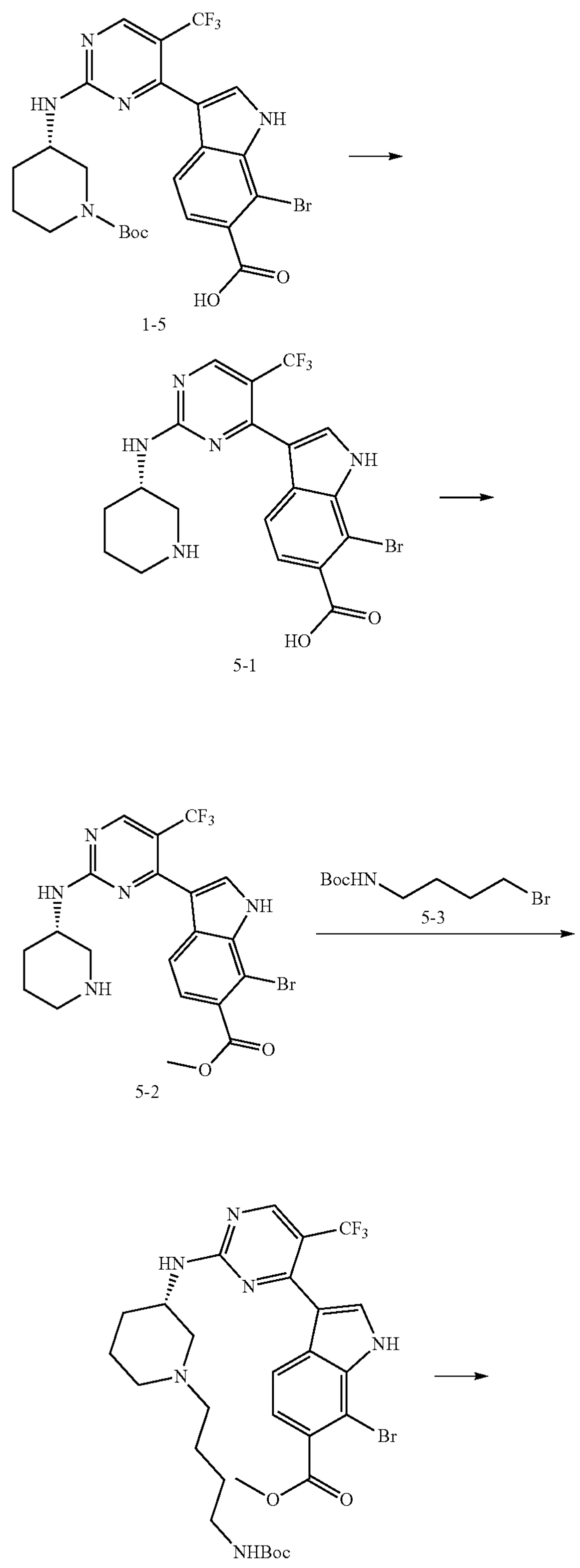

1-5

5-1

5-2

5-3

5-4

-continued

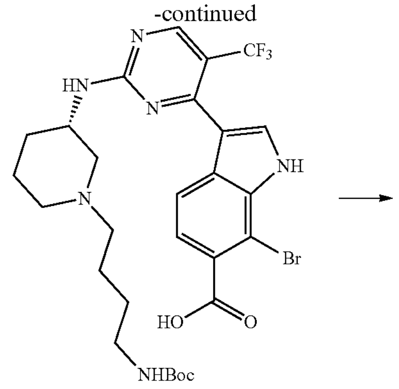

5-5

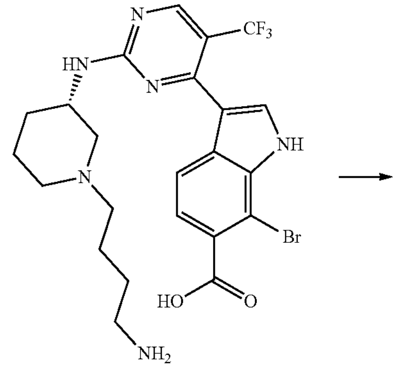

5-6

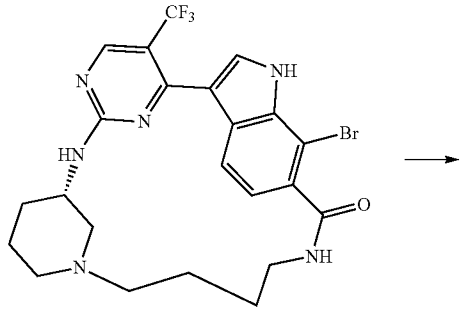

5-7

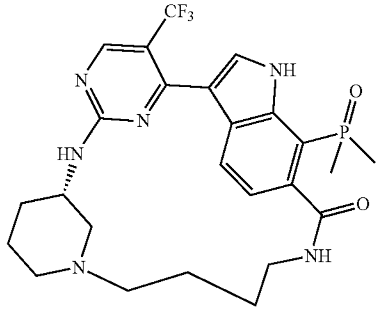

5

Step 1:

Hydrochloric acid/ethyl acetate (4 M, 4 mL) was added to a solution of compound 1-5 (0.5 g) in ethyl acetate (4 mL) at 20° C., and the mixture was stirred at 20° C. for 1 hour. After the reaction was completed, the reaction mixture was concentrated to obtain the crude product of the hydrochloride of compound 5-1. LCMS (ESI) m/z: 483.9, 485.9 (M+1).

Step 2:

Hydrochloric acid/methanol (4 M, 10 mL) was added to compound 5-1 (0.35 g) at 20° C., and the mixture was stirred at 50° C. for 12 hours. After the reaction was completed, the reaction mixture was concentrated to obtain compound 5-2. LCMS (ESI) m/z: 497.9, 499.9 ((M+1).

Step 3:

N,N-Diisopropylethylamine (297.27 mg) was added to a solution of compound 5-2 (0.41 g) and compound 5-3 (289.98 mg) in N,N-dimethylformamide (20 mL) at 20° C., and the mixture was stirred at 80° C. for 12 hours. Compound 5-3 (193.32 mg) and N,N-diisopropylethylamine (297.27 mg) were added to the reaction mixture, and the mixture was stirred at 100° C. for 4 hours. After the reaction was completed, the reaction mixture was poured into water (20 mL) and then extracted with ethyl acetate (20 mL*2). The combined organic phases were washed with water (20 mL) and saturated brine (20 mL), dried over anhydrous sodium sulfate, filtered, and concentrated to obtain a residue. The residue was purified by column chromatography (silica gel, eluent, petroleum ether:ethyl acetate=1:1 to 0:1) to obtain compound 5-4. LCMS (ESI) m/z: 669.0, 671.0 (M+1).

Step 4:

Sodium hydroxide (43.01 mg) was added to a solution of compound 5-4 (0.36 g) in methanol (12 mL) and water (4 mL) at 20° C., and the mixture was stirred at 50° C. for 12 hours. Sodium hydroxide (21.51 mg) was added to the reaction mixture, and the mixture was stirred at 50° C. for 12 hours. After the reaction was completed, the reaction mixture was concentrated to obtain a residue, and water (20 mL) was added to the residue. The aqueous phase was added with hydrochloric acid (1 mol/L) to adjust the pH to 5, and then extracted with ethyl acetate (50 mL*2). The combined organic phases were dried over anhydrous sodium sulfate, filtered, and the filtrate was concentrated to obtain compound 5-5. LCMS (ESI) m/z: 655.2, 657.2 (M+1).

Step 5:

Hydrochloric acid/ethyl acetate (4 M, 10 mL) was added to a solution of compound 5-5 (0.15 g) in ethyl acetate (10 mL) at 20° C., and the mixture was stirred at 20° C. for 0.5 hours. After the reaction was completed, the reaction mixture was concentrated to obtain the hydrochloride of compound 5-6. LCMS (ESI) m/z: 554.9, 556.9 (M+1).

Step 6:

o-(7-Azabenzotriazole-1-yl)-N,N,N,N-tetramethyluronium hexafluorophosphate (144.55 mg) and N,N-diisopropylethylamine (163.78 mg) were added to a solution of compound 5-6 (0.15 g) in N,N-dimethylformamide (30 mL) at 20° C., and the mixture was stirred at 20° C. for 2 hours. After the reaction was completed, the reaction mixture was poured into water (50 mL) and then extracted with ethyl acetate (30 mL*2). The combined organic phases were washed with water (50 mL) and saturated brine (50 mL), dried over anhydrous sodium sulfate, filtered, and concentrated to obtain a residue. The residue was purified by thin-layer chromatography (silica gel, ethyl acetate:methanol=1:1) to obtain compound 5-7. LCMS (ESI) m/z: 536.9, 538.9 (M+1).

Step 7:

Methanesulfonato[9,9-dimethyl-4,5-bis(diphenylphosphino)xanthene](2-methylamino-1,1-biphenyl-2-yl)palladium(II) (44.77 mg) and potassium phosphate (29.63 mg) were added to a solution of compound 5-7 (25 mg) and dimethylphosphine oxide (108.93 mg) in 1,4-dioxane (3 mL) at 20° C., and the mixture was stirred at 120° C. under nitrogen atmosphere for 20 hours. After the reaction was completed, the reaction mixture was filtered, the filter cake was washed with ethyl acetate (15 mL), and the filtrate was concentrated to obtain a residue. The residue was purified by preparative high performance liquid chromatography (column model: Waters Xbridge C18 150*50 mm*10 μm; mobile phase: [water ($NH_4HCO_3$)-acetonitrile]: 25% to 55%, 10 min) to obtain compound 5. LCMS (ESI) m/z: 535.3 (M+1).

$^1H$ NMR (400 MHz, $CD_3OD$) δ ppm 8.96 (br d, J=7.58 Hz, 1 H) 8.49 (s, 1 H) 8.08 (s, 1 H) 7.38 (dd, J=8.25, 3.48 Hz, 1 H) 3.90-4.04 (m, 1 H) 3.60-3.70 (m, 1 H) 3.04 (br d, J=10.39 Hz, 1 H) 2.84 (ddd, J=14.18, 9.90, 4.77 Hz, 1 H) 2.63 (ddd, J=14.06, 10.33, 5.81 Hz, 1 H) 2.02-2.12 (m, 5 H) 1.89-2.00 (m, 5 H) 1.73-1.87 (m, 3 H) 1.56-1.70 (m, 2 H) 1.39-1.54 (m, 2 H) 1.09-1.24 (m, 1 H).

Example 6

6

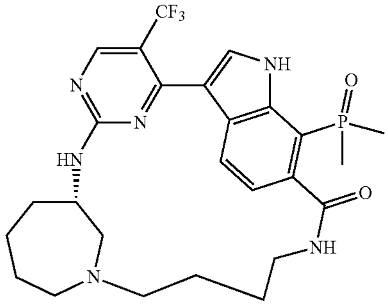

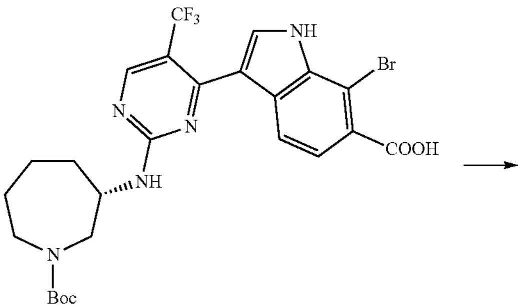

3-2

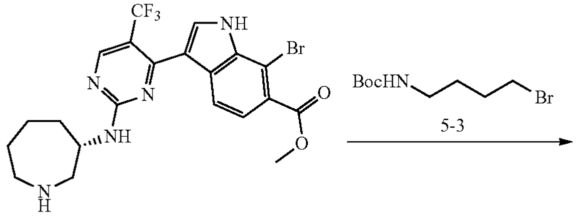

6-1

-continued

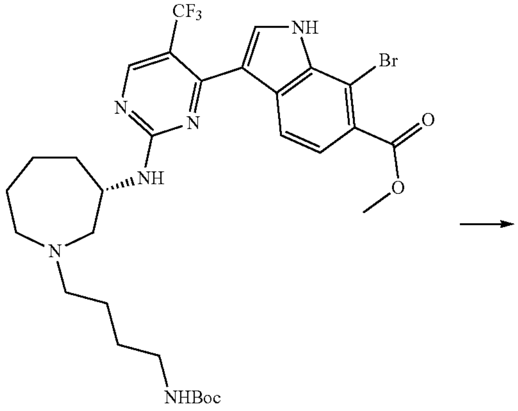

6-2

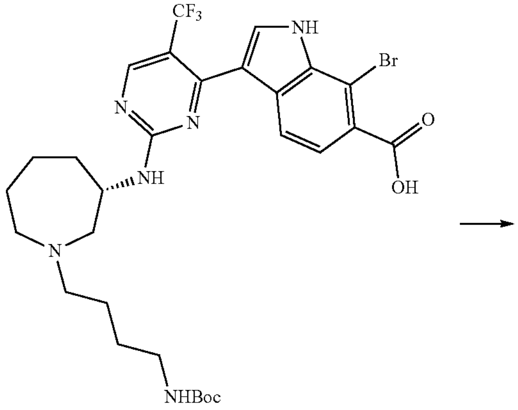

6-3

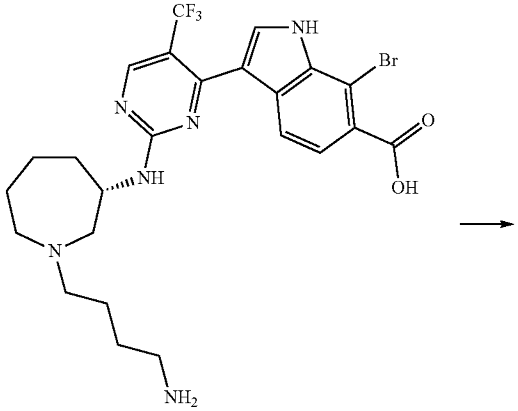

6-4

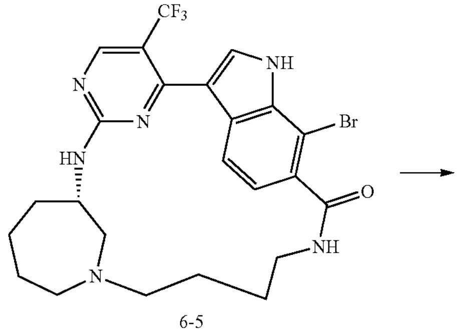

6-5

-continued

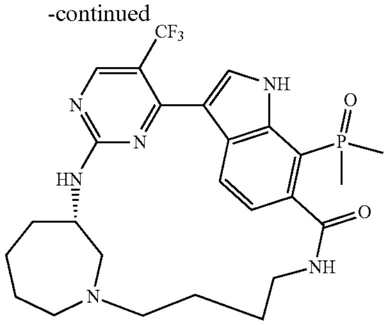

6

Step 1:

A hydrochloric acid/methanol (4 M, 30 mL) solution was added to compound 3-2 (1.5 g) at 20° C., and the mixture was stirred at 50° C. for 12 hours. After the reaction was completed, the reaction mixture was concentrated to obtain the hydrochloride of compound 6-1. LCMS (ESI) m/z: 512.1, 514.1 (M+1).

Step 2:

N,N-Diisopropylethylamine (824.28 mg) was added to a solution of the hydrochloride of compound 6-1 (0.7 g) and compound 5-3 (804.07 mg) in N,N-dimethylformamide (20 mL) at 20° C., and the mixture was stirred at 100° C. for 12 hours. After the reaction was completed, the reaction mixture was poured into water (30 mL) and then extracted twice with ethyl acetate (30 mL*2). The combined organic phases were washed with water (30 mL) and saturated brine (30 mL), dried over anhydrous sodium sulfate, filtered, and concentrated to obtain a residue. The residue was purified by column chromatography (silica gel, eluent, petroleum ether: ethyl acetate=2:1 to ethyl acetate:methanol=10:1) to obtain compound 6-2. LCMS (ESI) m/z: 683.1, 685.1 (M+1).

Step 3:

Sodium hydroxide (138.09 mg) was added to a solution of compound 6-2 (0.59 g) in methanol (15 mL) and water (5 mL) at 20° C., and the mixture was stirred at 60° C. for 12 hours. After the reaction was completed, the reaction mixture was concentrated to obtain a residue, and water (20 mL) was added to the residue. The aqueous phase was added with hydrochloric acid (1 mol/L) to adjust the pH to 5, and then extracted twice with ethyl acetate (20 mL*2). The combined organic phases were dried over anhydrous sodium sulfate, filtered, and concentrated to obtain compound 6-3. LCMS (ESI) m/z: 669.0, 671.0 (M+1).

Step 4:

Hydrochloric acid/ethyl acetate (4 M, 10 mL) was added to a solution of compound 6-3 (0.6 g) in ethyl acetate (10 mL) at 20° C., and the mixture was stirred at 20° C. for 0.5 hours. After the reaction was completed, the reaction mixture was concentrated to obtain the hydrochloride of compound 6-4. LCMS (ESI) m/z: 569.0, 571.0 (M+1).

Step 5:

o-(7-Azabenzotriazole-1-yl)-N,N,N,N-tetramethyluronium hexafluorophosphate (545.99 mg) and N,N-diisopropylethylamine (618.61 mg) were added to a solution of the hydrochloride of compound 6-4 (0.58 g) in N,N-dimethylformamide (300 mL) at 20° C., and the mixture was stirred at 20° C. for 0.5 hours. After the reaction was completed, the reaction mixture was poured into water (600 mL) and then extracted twice with ethyl acetate (150 mL*2). The combined organic phases were washed with water (200 mL*2) and saturated brine (200 mL), dried over anhydrous sodium sulfate, filtered, and concentrated to obtain a residue. The residue was purified by column chromatography (silica gel, eluent, petroleum ether:ethyl acetate=1:1 to ethyl acetate: methanol=7:1) to obtain compound 6-5. LCMS (ESI) m/z: 551.0, 553.0 (M+1).

Step 6:

Methanesulfonato[9,9-dimethyl-4,5-bis(diphenylphosphino)xanthene](2-methylamino-1,1-biphenyl-2-yl)palladium(II) (366.52 mg) and potassium phosphate (242.52 mg) were added to a solution of compound 6-5 (0.21 mg) and dimethylphosphine oxide (891.75 mg) in 1,4-dioxane (6 mL) at 20° C., and the mixture was stirred at 120° C. under nitrogen atmosphere for 16 hours. After the reaction was completed, the reaction mixture was filtered, the filter cake was washed with ethyl acetate (20 mL), and the filtrate was concentrated to obtain a residue. The residue was purified by preparative HPLC (column model: Waters Xbridge C18 150*50 mm*10 μm; mobile phase: [water ($NH_4HCO_3$)-acetonitrile]: 28% to 58%, 10 min) to obtain compound 6. LCMS (ESI) m/z: 549.3 (M+1).

$^1$H NMR (400 MHz, DMSO-d6) δ ppm 11.98 (br s, 1 H) 8.47-8.72 (m, 2 H) 7.90-8.16 (m, 2 H) 7.60-7.73 (m, 1 H) 7.13-7.23 (m, 1 H) 3.89-4.09 (m, 1 H) 3.18 (br dd, J=12.96, 4.03 Hz, 1 H) 2.84-2.98 (m, 1 H) 2.62-2.69 (m, 1 H) 2.06-2.39 (m, 5 H) 1.81-1.99 (m, 7 H) 1.69-1.80 (m, 2 H) 1.42-1.66 (m, 4 H) 1.35 (br d, J=1.96 Hz, 2 H) 1.00-1.17 (m, 1 H).

In Vitro Activity Assay

Experimental Example 1: In Vitro CDK7/CyclinT1 Enzyme Activity Assay

Experimental Materials:

CDK7/CyclinH/MAT1 was purchased from CARNA. Ulight-MBP peptide, Eu-MBP antibody, and 1× detection buffer were purchased from PerkinElmer. High-purity ATP was purchased from Promega. EDTA was purchased from Sigma. Nivo multimode microplate reader (PerkinElmer).

Experimental Methods:

Preparation of kinase buffer: the kinase buffer containing 50 mM HEPES, 1 mM EDTA, 10 mM $MgCl_2$, 0.01% Brij-35, pH 7.4.

2.38 g of HEPES, 58 mg of EDTA, 406 mg of $MgCl_2$, and 20 mg of Brij-35 were added to 200 mL of buffer, and the pH was adjusted to 7.4.

Preparation of Stop Solution:

100 μL of 1 M EDTA stock solution was mixed with 0.625 μL of 1× detection buffer and 1725 μL of distilled water to prepare the stop solution.

Enzyme, Ulight-MBP peptide, ATP, and inhibitors were diluted with the kinase buffer.

The Eu-MBP antibody was diluted to a concentration of 8 nM/L using detection buffer.

The compounds to be tested were 5-fold diluted with a multi-channel pipette to the 8th concentration, i.e., from 40 μM to 0.512 nM, with a final DMSO concentration of 4%. The experiment was set up in duplicate wells. 2.5 μL of each concentration gradient of the inhibitor was added to the microplate, followed by 5 μL of CDK7/CyclinH/MAT1 enzyme (5 ng), and 2.5 μL of a mixture of substrate and ATP (4 mM ATP, 50 nM Ulight-MBP peptide). At this point, the final concentration gradient of the compound was 10 μM diluted to 0.128 nM. The reaction system was reacted at 25° C. for 60 minutes. After the reaction, 5 μL of stop solution was added to each well, and the reaction was continued at 25° C. for 5 minutes. After stopping the reaction, 5 μL of Eu-MBP antibody dilution was added to each well, and the mixture was reacted at 25° C. for 60 minutes. Data were then collected using the PerkinElmer Nivo multimode microplate reader in TR-FRET mode (excitation wavelength: 320 nm, emission wavelength: 665 nm).

Data Analysis:

Using the equation (Sample−Min)/(Max−Min)*100% to convert the raw data into inhibition rate, the $IC_{50}$ value may be obtained by curve fitting with four parameters (obtained by "log (inhibitor) vs. response—Variable slope" mode in GraphPad Prism). Table 1 provides the CDK7/CyclinH/MAT1 enzymatic inhibitory activity of the compounds of the present disclosure.

Experimental conclusion: The compounds of the present disclosure exhibit good activity against CDK7 kinase.

Experimental Example 2: In Vitro CDK2/CyclinB1 Enzyme Activity Assay

Experimental Materials:

CDK2/CyclinE1 was purchased from SignalChem. Ulight-4E-BP1 peptide, Eu-anti-phospho-tyrosine antibody, and 1× detection buffer were purchased from PerkinElmer. High-purity ATP was purchased from Promega. EDTA was purchased from Sigma. Nivo multimode microplate reader (PerkinElmer).

Experimental Methods:

Preparation of kinase buffer: the kinase buffer containing 50 mM HEPES, 1 mM EDTA, 10 mM $MgCl_2$, 0.01% Brij-35, pH 7.4.

2.38 g of HEPES, 58 mg of EDTA, 406 mg of $MgCl_2$, and 20 mg of Brij-35 were added to 200 mL of buffer, and the pH was adjusted to 7.4.

Preparation of Stop Solution:

100 μL of 1 M EDTA stock solution was mixed with 0.625 μL of 1× detection buffer and 1725 μL of distilled water to prepare the stop solution.

Enzyme, Ulight-4E-BP1 peptide, ATP, and inhibitors were diluted with the kinase buffer.

The Eu-anti-phospho-tyrosine antibody was diluted to a concentration of 8 nM/L using detection buffer.

The compounds to be tested were 5-fold diluted with a multi-channel pipette to the 8th concentration, i.e., from 40 μM to 0.512 nM, with a final DMSO concentration of 4%. The experiment was set up in duplicate wells. 2.5 μL of each concentration gradient of the inhibitor was added to the microplate, followed by 5 μL of CDK2/CyclinE1 enzyme (10 ng), and 2.5 μL of a mixture of substrate and ATP (4 mM ATP, 100 nM Ulight-4E-BP1 peptide). At this point, the final concentration gradient of the compound was 10 μM diluted to 0.128 nM. The reaction system was reacted at 25° C. for 120 minutes. After the reaction, 5 μL of stop solution was added to each well, and the reaction was continued at 25° C. for 5 minutes. After stopping the reaction, 5 μL of Eu-anti-phospho-tyrosine antibody dilution was added to each well, and the mixture was reacted at 25° C. for 60 minutes. Data were then collected using the PerkinElmer Nivo multimode microplate reader in TR-FRET mode (excitation wavelength: 320 nm, emission wavelength: 665 nm).

Data Analysis:

Using the equation (Sample−Min)/(Max−Min)*100% to convert the raw data into inhibition rate, the $IC_{50}$ value may be obtained by curve fitting with four parameters (obtained by "log (inhibitor) vs. response—Variable slope" mode in GraphPad Prism). Table 1 provides the CDK2/CyclinE1 enzymatic inhibitory activity of the compounds of the present disclosure.

Experimental conclusion: The compounds of the present disclosure do not have strong inhibitory activity against CDK2 kinase.

Experimental Example 3: In Vitro CDK9/CyclinE1 Enzyme Activity Assay

Experimental Materials:

CDK9-CyclinT1 was purchased from CARNA. Ulight-4E-BP1 peptide, Eu-anti-phospho-tyrosine antibody, and 1× detection buffer were purchased from PerkinElmer. High-purity ATP was purchased from Promega. EDTA was purchased from Sigma. Nivo multimode microplate reader (PerkinElmer).

Experimental Methods:

Preparation of kinase buffer: the kinase buffer containing 50 mM HEPES, 1 mM EDTA, 10 mM $MgCl_2$, 0.01% Brij-35, pH 7.4.

2.38 g of HEPES, 58 mg of EDTA, 406 mg of $MgCl_2$, and 20 mg of Brij-35 were added to 200 mL of buffer, and the pH was adjusted to 7.4.

Preparation of Stop Solution:

100 μL of 1 M EDTA stock solution was mixed with 0.625 μL of 1× detection buffer and 1725 μL of distilled water to prepare the stop solution.

Enzyme, Ulight-4E-BP1 peptide, ATP, and inhibitors were diluted with the kinase buffer.

The Eu-anti-phospho-tyrosine antibody was diluted to a concentration of 8 nM/L using detection buffer.

The compounds to be tested were 4-fold diluted with a multi-channel pipette to the 8th concentration, i.e., from 400 μM to 24.4 nM, with a final DMSO concentration of 4%. The experiment was set up in duplicate wells. 2.5 μL of each concentration gradient of the inhibitor was added to the microplate, followed by 5 μL of CDK9-CyclinT1 enzyme (2 ng), and 2.5 μL of a mixture of substrate and ATP (8 mM ATP, 50 nM Ulight-4E-BP1 peptide). At this point, the final concentration gradient of the compound was 100 μM diluted to 6.1 nM. The reaction system was reacted at 25° C. for 120 minutes. After the reaction, 5 μL of stop solution was added to each well, and the reaction was continued at 25° C. for 5 minutes. After stopping the reaction, 5 μL of Eu-anti-phospho-tyrosine antibody dilution was added to each well, and the mixture was reacted at 25° C. for 60 minutes. Data were then collected using the PerkinElmer Nivo multimode microplate reader in TR-FRET mode (excitation wavelength: 320 nm, emission wavelength: 665 nm).

Data Analysis:

Using the equation (Sample−Min)/(Max−Min)*100% to convert the raw data into inhibition rate, the $IC_{50}$ value may be obtained by curve fitting with four parameters (obtained by "log (inhibitor) vs. response—Variable slope" mode in GraphPad Prism). Table 1 provides the CDK9-CyclinT1 enzymatic inhibitory activity of the compounds of the present disclosure.

Experimental conclusion: The compounds of the present disclosure do not have strong inhibitory activity against CDK9 kinase.

Experimental Example 4: In Vitro HCC70 Cell Activity Assay

Experimental Materials:

1640 culture medium, fetal bovine serum, penicillin/streptomycin antibiotics were purchased from WISENT. CellTiter-Glo (cell viability chemiluminescence detection reagent) reagent was purchased from Promega. HCC70 cell line was purchased from Nanjing Cobioer Biosciences Co. Ltd. Nivo multimode microplate reader (PerkinElmer).

Experimental Methods:

The HCC70 cells were seeded in a white 96-well plate, with 80 μL of cell suspension per well, containing 6000 HCC70 cells each. The cell plate was incubated overnight in a $CO_2$ incubator. The compounds to be tested were 3-fold diluted with a multi-channel pipette to the 8th concentration, i.e., diluted from 2 mM to 304 nM, and the experiment was set up in duplicate wells. 78 μL of culture medium was added to an intermediate plate, and then 2 μL of gradient diluted compound per well was transferred to the intermediate plate according to the corresponding position. After mixing well, the compound was transferred to the cell plate at 20 μL per well. The concentration of the compound transferred to the cell plate ranged from 10 μM to 1.52 nM. The cell plate was incubated in a $CO_2$ incubator for 4 days. Another cell plate was prepared to measure the signal on the day of drug addition as the maximum value (denoted as Max in the equation below) for data analysis. 25 μL of cell viability chemiluminescence detection reagent was added to each well of this cell plate, and incubated at room temperature for 10 minutes to stabilize the luminescent signal. A multimode microplate reader was used for reading.

25 μL of cell viability chemiluminescence detection reagent was added to each well of this cell plate, and incubated at room temperature for 10 minutes to stabilize the luminescent signal. A multimode microplate reader was used for reading.

Data Analysis:

Using the equation (Sample−Min)/(Max−Min)*100% to convert the raw data into inhibition rate, the $IC_{50}$ value may be obtained by curve fitting with four parameters (obtained by "log (inhibitor) vs. response—Variable slope" mode in GraphPad Prism). Table 1 provides the inhibitory activity of the compounds of the present disclosure on the proliferation of HCC70 cells.

Experimental conclusion: The compounds of the present disclosure exhibit strong inhibitory activity on HCC70 cells.

Experimental Example 5: In Vitro OVCAR3 Cell Activity Assay

Experimental Materials:

1640 culture medium, fetal bovine serum, penicillin/streptomycin antibiotics were purchased from WISENT. CellTiter-Glo (cell viability chemiluminescence detection reagent) reagent was purchased from Promega. OVCAR3 cell line was purchased from Nanjing Cobioer Biosciences Co. Ltd. Nivo multimode microplate reader (PerkinElmer).

Experimental Methods:

The OVCAR3 cells were seeded in a white 96-well plate, with 80 μL of cell suspension per well, containing 2000 OVCAR3 cells each. The cell plate was incubated overnight in a $CO_2$ incubator.

The compounds to be tested were 5-fold diluted with a multi-channel pipette to the 8th concentration, i.e., diluted from 200 μM to 0.512 nM, and the experiment was set up in duplicate wells. 78 μL of culture medium was added to an intermediate plate, and then 2 μL of gradient diluted compound per well was transferred to the intermediate plate according to the corresponding position. After mixing well, the compound was transferred to the cell plate at 20 μL per well. The concentration of the compound transferred to the cell plate ranged from 1 μM to 0.0026 nM. The cell plate was incubated in a $CO_2$ incubator for 3 days. Another cell plate was prepared to measure the signal on the day of drug addition as the maximum value (denoted as Max in the equation below) for data analysis. 25 μL of cell viability chemiluminescence detection reagent was added to each well of this cell plate, and incubated at room temperature for 10 minutes to stabilize the luminescent signal. A multimode microplate reader was used for reading.

25 μL of cell viability chemiluminescence detection reagent was added to each well of this cell plate, and incubated at room temperature for 10 minutes to stabilize the luminescent signal. A multimode microplate reader was used for reading.

Data Analysis:

Using the equation (Sample−Min)/(Max−Min)*100% to convert the raw data into inhibition rate, the $IC_{50}$ value may be obtained by curve fitting with four parameters (obtained by "log (inhibitor) vs. response—Variable slope" mode in GraphPad Prism). Table 1 provides the inhibitory activity of the compounds of the present disclosure on the proliferation of OVCAR3 cells.

Experimental conclusion: The compounds of the present disclosure exhibit strong inhibitory activity on OVCAR3 cells.

TABLE 1

Summary of results of experimental examples 1 to 5

| Test compound | CDK7 $IC_{50}$ (nM) | CDK2 $IC_{50}$ (nM) | CDK9 $IC_{50}$ (nM) | HCC70 cell $IC_{50}$ (nM) | OVCAR3 cell $IC_{50}$ (nM) |
|---|---|---|---|---|---|
| Formate of compound 1 | 1.0 | 253.3 | 723 | <1.5 | 0.3 |
| Compound 3 | 1.1 | >1000 | >1000 | 1.4 | 0.6 |
| Compound 4 | 1.6 | >1000 | >1000 | 0.6 | 0.2 |
| Compound 5 | 1.2 | 738 | >1000 | 1.0 | 0.2 |
| Compound 6 | 1.4 | >1000 | >1000 | 1.8 | 0.6 |

Experimental Example 6: In Vivo Efficacy Study

In vivo efficacy experiments were conducted on BALB/c nude mice subcutaneously implanted with human tumor cell line-based xenograft (CDX) derived from HCC70 breast cancer patients.

Experimental Operation:

BALB/c nude mice, female, 6 to 8 weeks old, weighing approximately 19 to 23 g, were maintained in a special pathogen-free environment in individual ventilated cages (6 mice per cage). All cages, bedding, and water were disinfected before use. All animals had free access to a standard certified commercial laboratory diet. A total of 36 mice, purchased from the Laboratory Animal Department of the Shanghai Institute of Planned Parenthood Research (formerly Shanghai SIPPR-BK), were used for the study. Each mouse was injected with $10\times10^6$ HCC70 cells on the right side of the neck, with an injection volume of 0.2 mL, and the cell suspension was in a 1:1 ratio of PBS and Matrigel. When the average tumor volume reached approximately 179 $mm^3$, random grouping was performed, and dosing was initiated. The dosing was 3 mg/kg. Tumor volume was measured twice a week with a two-dimensional caliper, and the volume was measured in $mm^3$ and calculated by the following equation: $V=0.5a\times b^2$, where a and b are the long and short diameters of the tumor, respectively. The experimental results are as shown in Table 2.

TABLE 2

| Experimental results of in vivo efficacy study | | | | | | |
|---|---|---|---|---|---|---|
| | Dose | Animal | Tumor volume ($mm^3$) | | | |
| Compound | (mg/kg) | tolerance | Day 0 | Day 7 | Day 14 | Day 21 |
| Blank control (5% DMSO + 95% (10% HP-β-CD)) | 0 | Good | 179 | 369 | 582 | 1130 |
| Formate of compound 1 | 1.5 | Good | 179 | 273 | 178 | 105 |
| Compound 5 | 3 | Good | 179 | 260 | 305 | 230 |
| Compound 6 | 3 | Good | 179 | 272 | 344 | 403 |

Experimental conclusion: The compounds of the present disclosure exhibit good efficacy and safety in the HCC70 breast cancer CDX in vivo efficacy model.

What is claimed is:

1. A compound of formula (II) or a pharmaceutically acceptable salt thereof, (II)

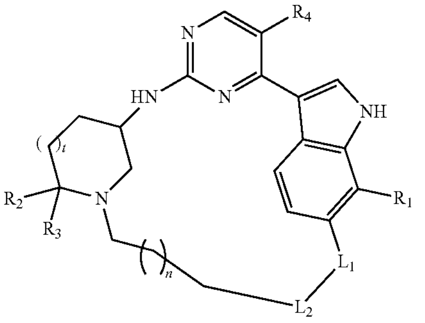

wherein $R_1$ is selected from H, CN, F, Cl, Br, I, $C_{1-3}$ alkyl, —$OC_{1-3}$ alkyl, $C_{3-6}$ cycloalkyl, $S(O)_mR_a$, $P(X)R_cR_d$, $C(O)R_a$, $S(O)_mNR_aR_b$, and $C(O)NR_aR_b$, and the $C_{1-3}$ alkyl, —$OC_{1-3}$ alkyl, and $C_{3-6}$ cycloalkyl are optionally substituted by 1, 2, or 3 R;

$R_a$ is selected from $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl, $R_b$ is selected from H and $C_{1-3}$ alkyl, and the $C_{1-3}$ alkyl, —$OC_{1-3}$ alkyl, —$NHC_{1-3}$ alkyl, —$N(C_{1-3}$ alkyl$)_2$, and $C_{3-6}$ cycloalkyl are optionally substituted by 1, 2, or 3 R;

$R_c$ and $R_d$ are independently selected from $C_{1-3}$ alkyl and $OC_{1-3}$ alkyl, or $R_c$ and $R_d$ together with the P atom to which they are attached form a 4- to 6-membered heterocycloalkyl ring, and the —$OC_{1-3}$ alkyl, $C_{1-3}$ alkyl, and 4- to 6-membered heterocycloalkyl ring are optionally substituted by 1, 2, or 3 R;

X is selected from O and S;

$L_1$ is selected from —$CH_2$—, —O—, —$NR_e$—, —C(O)—, —$S(O)_q$—, and —P(O)—;

$L_2$ is selected from —$CH_2$—, —O—, and —$NR_e$—;

$R_e$ is selected from H and $C_{1-3}$ alkyl, and the $C_{1-3}$ alkyl is optionally substituted by 1, 2, or 3 R;

$R_2$ and $R_3$ are each independently selected from H, $C_{1-3}$ alkyl, and $C_{2-4}$ alkenyl, or $R_2$ and $R_3$ together with the C atom to which they are attached form a $C_{3-6}$ cycloalkyl ring or a 3- to 6-membered heterocycloalkyl ring, and the $C_{1-3}$ alkyl, $C_{2-4}$ alkenyl, $C_{3-6}$ cycloalkyl ring, and 3- to 6-membered heterocycloalkyl ring are optionally substituted by 1, 2, or 3 R;

$R_4$ is selected from $C_{1-3}$ haloalkyl, CN, F, Cl, Br, and I;

R is independently selected from F, Cl, Br, $NH_2$, and CN;

n is selected from 0, 1, 2, 3, 4, and 5;

m and q are independently selected from 1 and 2;

t is selected from 0, 1, 2, and 3.

2. The compound or the pharmaceutically acceptable salt thereof according to claim 1, wherein $R_1$ is selected from $S(O)_mR_a$, and the $S(O)_mR_a$ is selected from

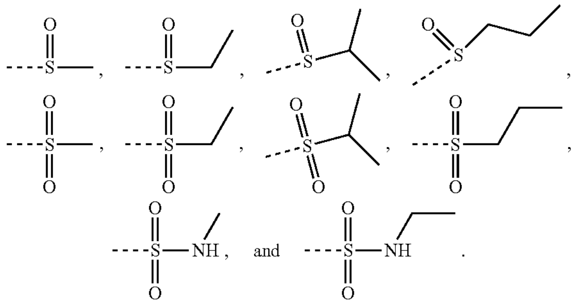

3. The compound or the pharmaceutically acceptable salt thereof according to claim 1, wherein $R_1$ is selected from $P(X)R_cR_d$, the $P(X)R_cR_d$ is selected from

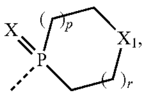

$X_1$ is selected from $CH_2$, O, and NH, p is selected from 0 and 1, and r is selected from 0 and 1.

4. The compound or the pharmaceutically acceptable salt thereof according to claim 3, wherein the

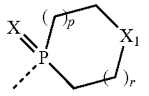

is selected from

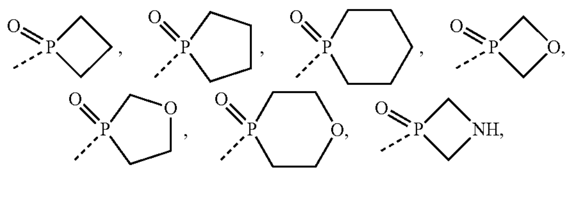

-continued

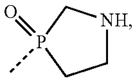

and

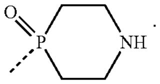

5. The compound or the pharmaceutically acceptable salt thereof according to claim 1, wherein $R_1$ is selected from

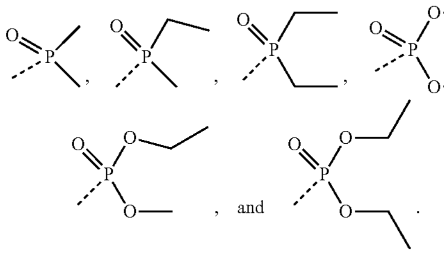

6. The compound or the pharmaceutically acceptable salt thereof according to claim 1, wherein $R_1$ is selected from $C(O)R_a$, and the $C(O)R_a$ is selected from

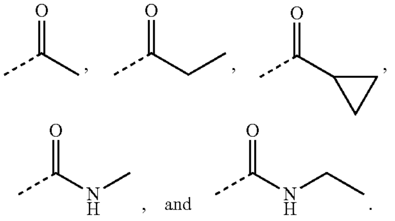

7. The compound or the pharmaceutically acceptable salt thereof according to claim 1, wherein $R_1$ is selected from

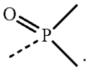

8. The compound or the pharmaceutically acceptable salt thereof according to claim 1, wherein $R_2$ and $R_3$ are each independently selected from H, methyl, ethyl, n-propyl, and isopropyl, or $R_2$ and $R_3$ together with the C atom to which they are attached form a cyclopropyl ring, a cyclobutyl ring, a cyclopentyl ring, and a cyclohexyl ring.

9. The compound or the pharmaceutically acceptable salt thereof according to claim 8, wherein $R_2$ and $R_3$ are each independently selected from H and methyl; or, $R_2$ and $R_3$ together with the C atom to which they are attached form a cyclopropyl ring.

10. The compound or the pharmaceutically acceptable salt thereof according to claim 1, wherein $R_4$ is selected from $CF_3$ and CN;

or, $L_1$ is selected from $—CH_2—$, —O—, $—NR_e—$, —C(O)—, —S(O)—, $—S(O)_2—$, and —P(O)—.

11. The compound or the pharmaceutically acceptable salt thereof according to claim 1, wherein the structural moiety

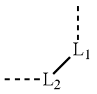

is selected from

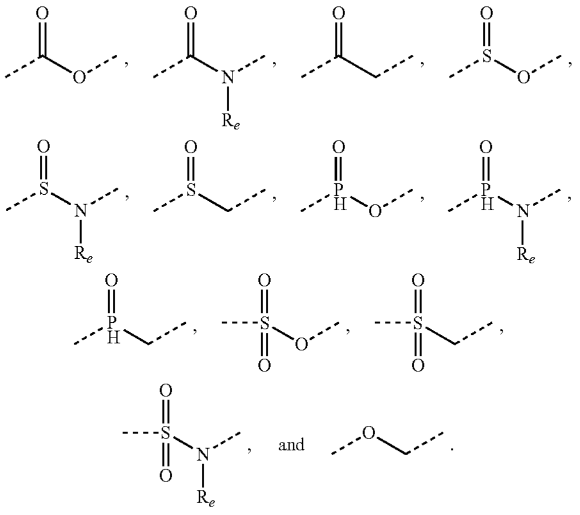

12. The compound or the pharmaceutically acceptable salt thereof according to claim 11, wherein the structural moiety

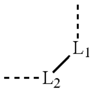

is selected from

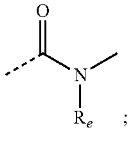

or, the structural moiety

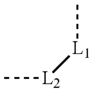

is selected from

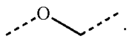

13. The compound or the pharmaceutically acceptable salt thereof according to claim 12, wherein the structural moiety

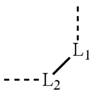

is selected from

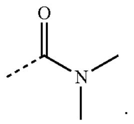

14. The compound or the pharmaceutically acceptable salt thereof according to claim 1, wherein the compound is selected from:

(I-1)

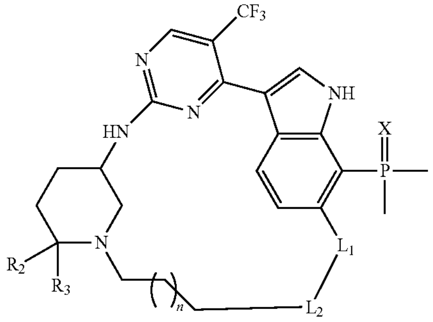

, (I-2)

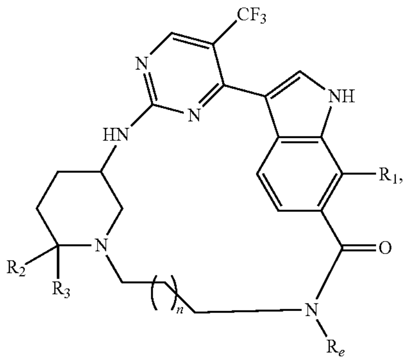

and (II-1)

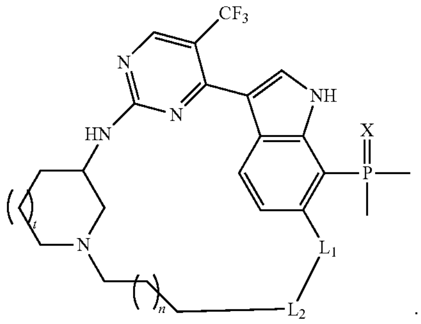

.

15. The compound or the pharmaceutically acceptable salt thereof according to claim 14, wherein the compound is selected from:

(II-1-1)

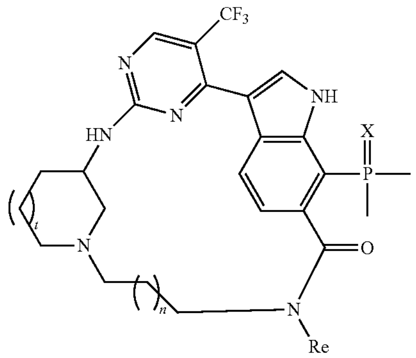

and (II-1-2)

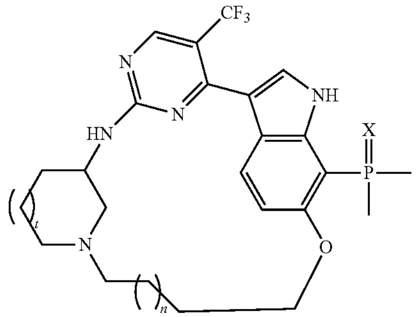

.

16. The compound or the pharmaceutically acceptable salt thereof according to claim 1, wherein $R_e$ is selected from hydrogen and methyl.

17. A compound of the following formula or a pharmaceutically acceptable salt thereof, selected from

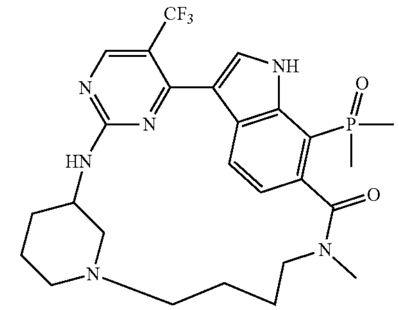

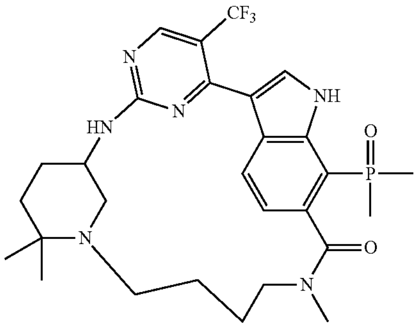

-continued
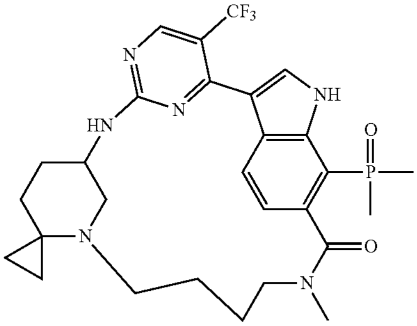
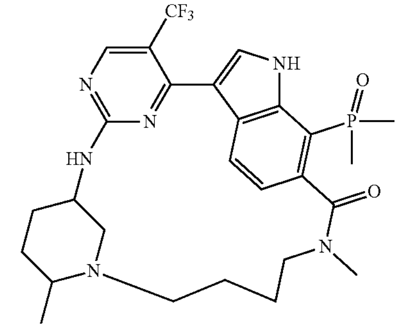
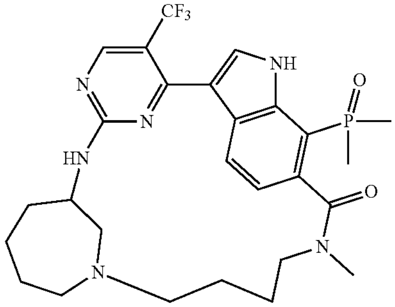
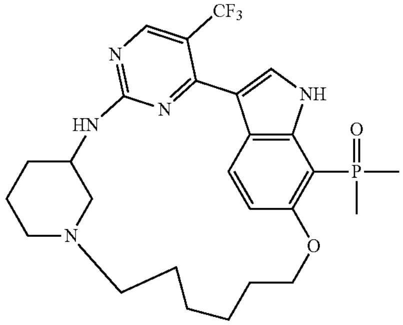
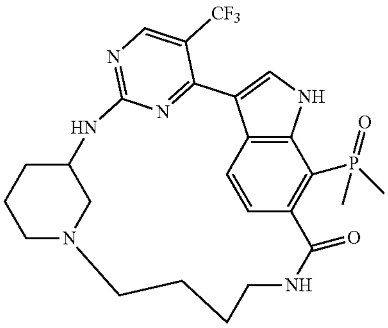
and
-continued
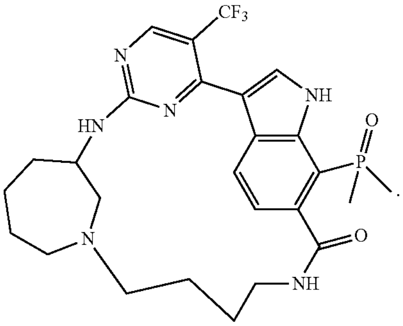
18. A compound of the following formula or a pharmaceutically acceptable salt thereof, selected from
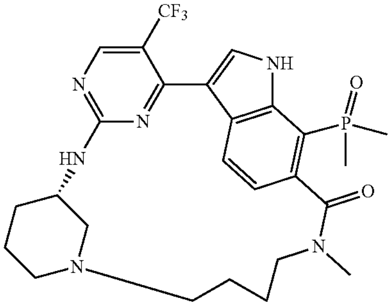
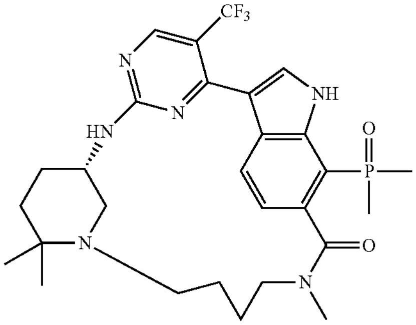
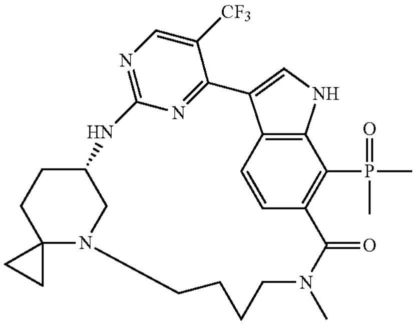

-continued
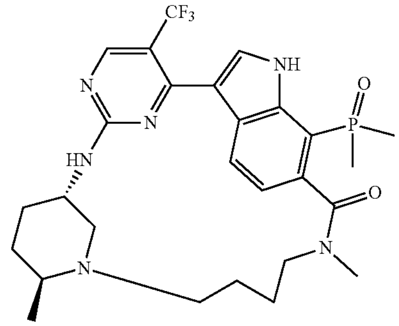
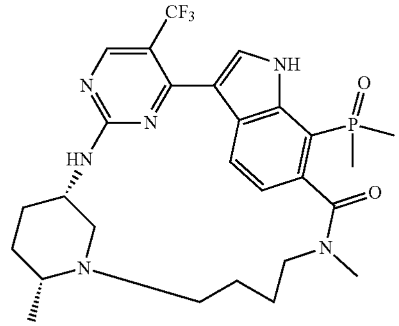
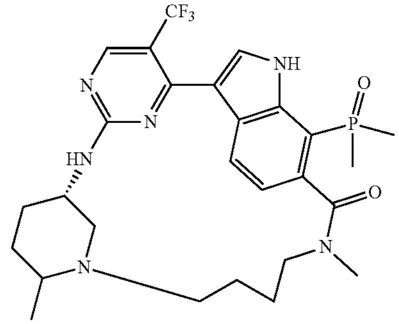
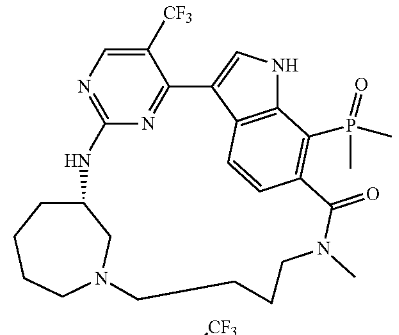
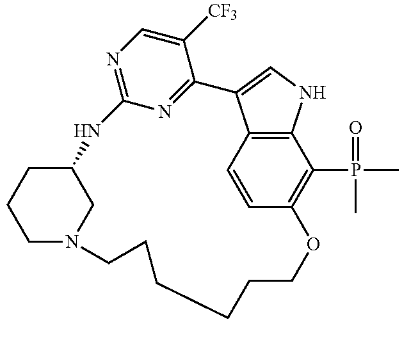
-continued
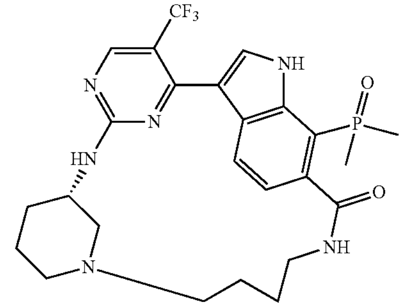
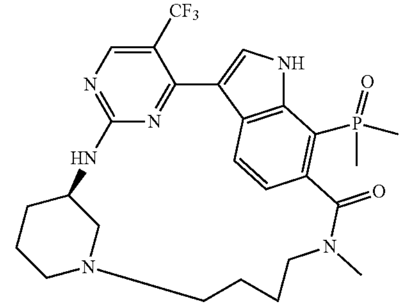
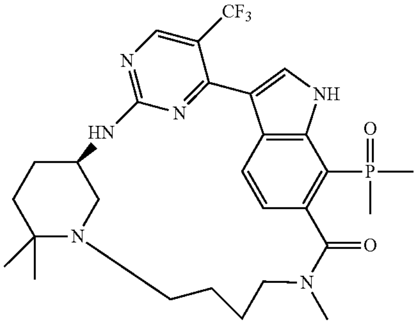
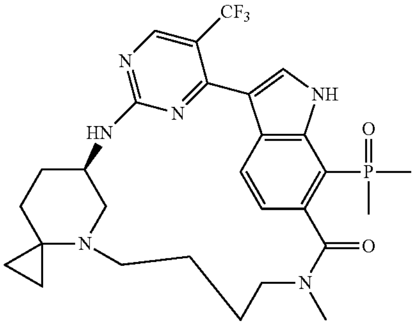
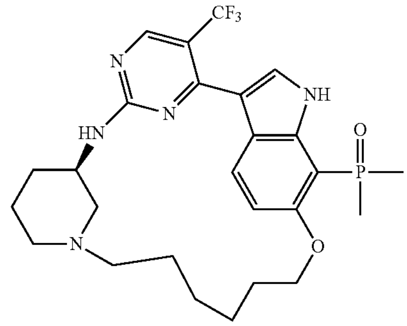

-continued
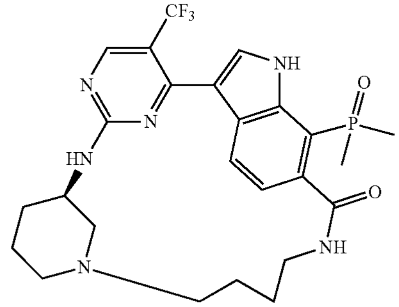
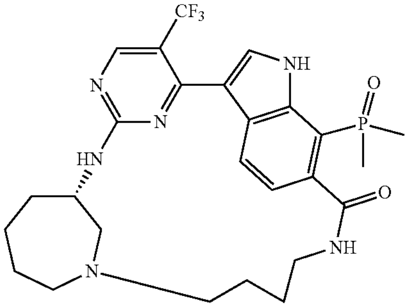
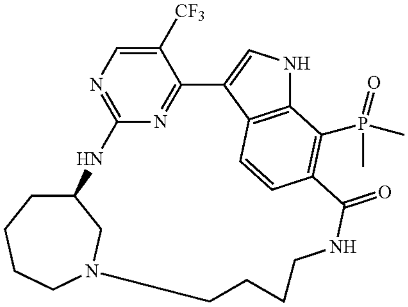
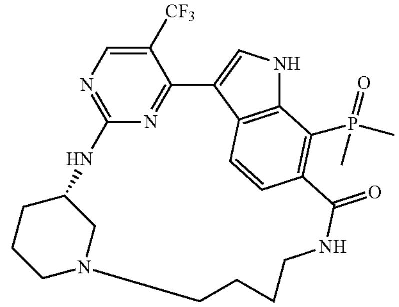
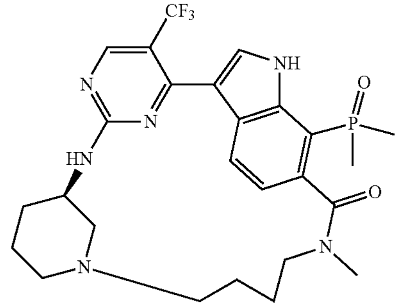
-continued
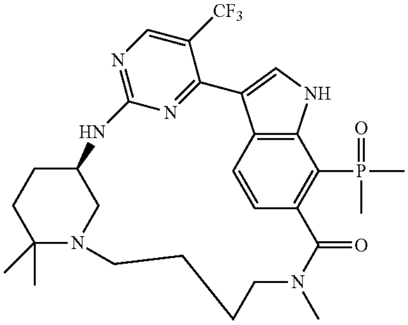
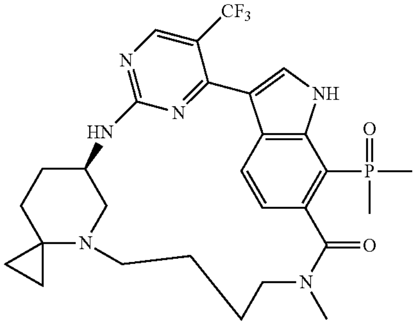
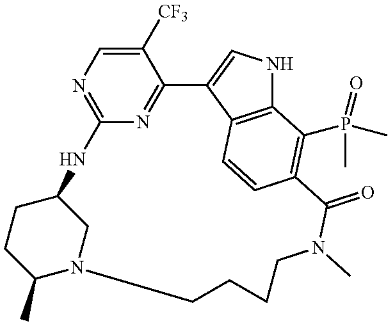
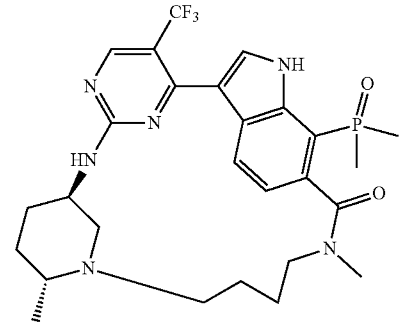
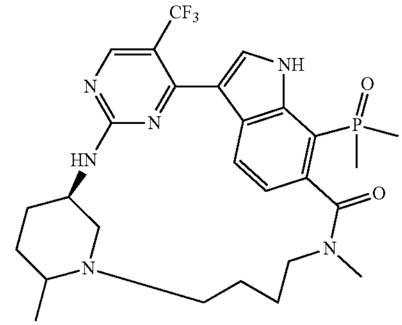

-continued

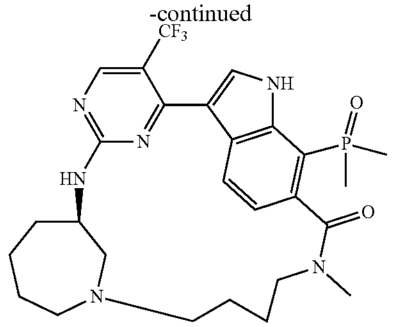

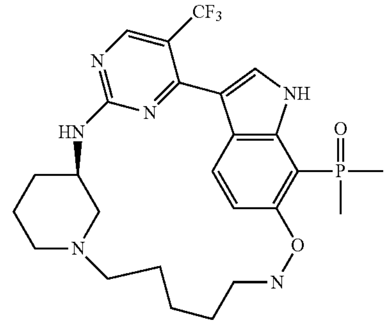

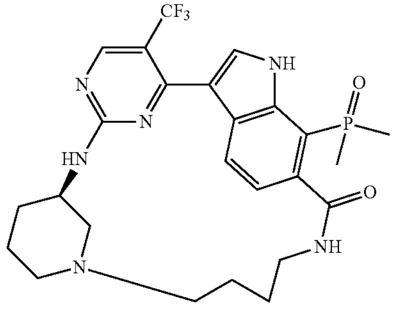

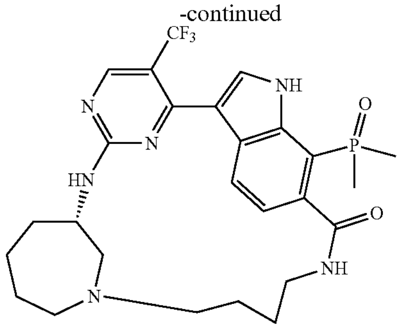

and

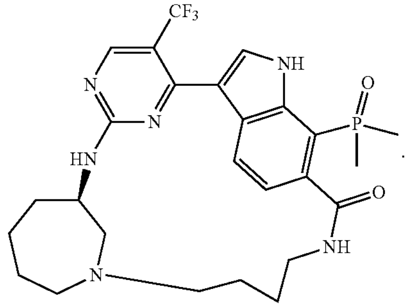

19. A method for inhibiting CDK7 in a subject in need thereof, comprising: administering a therapeutically effective amount of the compound or the pharmaceutically acceptable salt thereof according to claim 1 to the subject.

20. A method for treating breast cancer in a subject in need thereof, comprising: administering a therapeutically effective amount of the compound or the pharmaceutically acceptable salt thereof according to claim 1 to the subject.

* * * * *